United States Patent [19]

Akimoto et al.

[11] Patent Number: 5,539,113

[45] Date of Patent: Jul. 23, 1996

[54] PYRROLOPYRIMIDINE DERIVATIVES, THEIR PRODUCTION

[75] Inventors: Hiroshi Akimoto, Kobe; Takenori Hitaka, Takarazuka; Tetsuo Miwa, Kobe, all of Japan

[73] Assignee: Takeda Chemical Industries, Ltd., Osaka, Japan

[21] Appl. No.: 161,533

[22] Filed: Dec. 6, 1993

Related U.S. Application Data

[62] Division of Ser. No. 824,106, Jan. 22, 1992, Pat. No. 5,296,600, which is a division of Ser. No. 578,258, Sep. 6, 1990, Pat. No. 5,106,974, which is a division of Ser. No. 326,901, Mar. 21, 1989, Pat. No. 4,997,838.

[30] Foreign Application Priority Data

Mar. 24, 1988 [JP] Japan .................................. 63-71149
Sep. 29, 1988 [JP] Japan .................................. 63-245379

[51] Int. Cl.$^6$ ................................................ C07D 487/02
[52] U.S. Cl. .................................................... 544/280
[58] Field of Search ............................. 514/258; 544/280

[56] References Cited

U.S. PATENT DOCUMENTS

| | | | |
|---|---|---|---|
| 4,532,241 | 7/1985 | DeGraw et al. | 514/258 |
| 4,684,653 | 8/1987 | Taylor et al. | 514/258 |
| 4,997,838 | 3/1990 | Akimoto et al. | 514/258 |
| 5,106,974 | 4/1992 | Akimoto et al. | 544/280 |

FOREIGN PATENT DOCUMENTS 334636 9/1989 European Pat. Off. .

OTHER PUBLICATIONS

*Journal of Medicinal Chemistry,* vol. 28, 914–921 (1985) Taylor et al.
*Journal of Medicinal Chemistry,* Winstock et al., 13(5), 1970, 995–997.
CA 99:70481 A, 1983 Nishimura et al.

Primary Examiner—Mukund J. Shah
Assistant Examiner—Matthew V. Grumbling
Attorney, Agent, or Firm—Foley & Lardner

[57] ABSTRACT

A process of making a compound of the formula

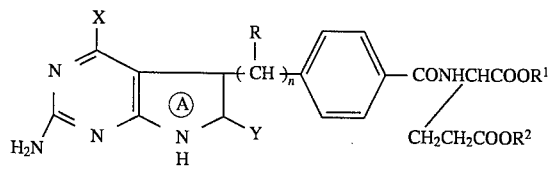

wherein the ring Ⓐ is a pyrrole or pyrroline ring, X is an amino group or a hydroxyl group, Y is a hydrogen atom, an amino group or a hydroxyl group, R is a hydrogen atom, a fluorine atom, an alkyl group, an alkenyl group or an alkynyl group, —COOR$^1$ and —COOR$^2$ are independently carboxyl groups which may be esterified and n is an integer of 2 to 4, and R may be different in each of the n repeating units, and salts thereof have excellent antitumor effects, and can be used as antitumor agents in mammals.

1 Claim, No Drawings

PYRROLOPYRIMIDINE DERIVATIVES, THEIR PRODUCTION

This application is a division of Ser. No. 07/824,106 filed Jan. 22, 1992, now U.S. Pat. No. 5,296,600 which is a division of Ser. No. 07/578,258 filed Sep. 6, 1990, now U.S. Pat. No. 5,106,974; which is a division of Ser. No. 07/326,901 filed Mar. 21, 1989 now U.S. Pat. No. 4,997,838.

This invention relates to the novel pyrrolopyrimidine derivatives which are useful as anti-tumor agents, the production and utilization thereof.

Folic acid is a carrier of a C1 unit in a living body, derived from formic acid or formaldehyde, acting as a coenzyme in various enzymatic reactions such as those in biosynthesis of nucleic acid, in metabolism of amino acids and peptides and in generation of methane. Particularly in biosynthesis of nucteic acid, folic acid is essential for formylation in the two pathways, i.e. the purine synthetic pathway and the thymidine synthetic pathway. Usually folic acid is required to be transformed into its activated coenzyme form by reduction in two steps before it becomes biologically active. Amethopterin (methotrexate: MTX) and the related compounds are known to inhibit the reduction from dihydrofolic acid into tetrahydrofolic acid by coupling strongly with the dominant enzyme in the second step (dihydrofolic acid reductase). These drugs have been developed as antitumor drugs because they may disturb the DNA synthesis and consequently cause cell death, and are currently regarded of major clinical important. On the other hand, a novel tetrahydroaminopterin antitumor agent (5,10-dideaza-5,6,7,8-tetrahydroaminopterin: DDATHF) has been reported which, unlike the drugs described above, does not inhibit dihydrofolic acid reductase and the main mechanism of which consists in inhibition of glycinamide ribonucleotide transformylase required in the initial stage of purine biosynthesis [Journal of Medicinal Chemistry, 28, 914 (1985)].

Various studies are now being conducted on therapy for cancer, and what is expected strongly is the development of drugs which are more effective and have toxicities highly specific to cancer cells based on some new mechanism. The antitumor agent MTX, the action mechanism of which consists in antagonism against folic acid, is clinically used widely, though the therapeutic effect is still unsatisfactory because it has relatively strong toxicity with little effect on solid cancer.

As the result of the inventors' researches under the circumstances described above, they have found out that novel pyrrolopyrimidine derivatives have toxicities highly specific to tumor cells and excellent antitumor effects, and completed this invention.

This invention relates to (1) A compound of the formula (I)

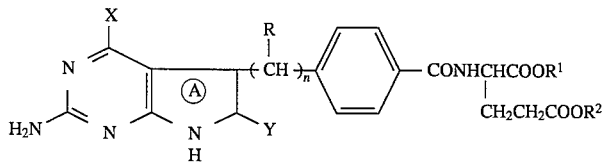

wherein the ring Ⓐ is a pyrrole or pyrroline ring, X is an amino group or a hydroxyl group, Y is a hydrogen atom, an amino group or a hydroxyl group, R is a hydrogen atom, a fluorine atom, an alkyl group, an alkenyl group or an alkynyl group, $-COOR^1$ and $-COOR^2$ are independently carboxyl groups which may be esterified and n is an integer of 2 to 4, and R may be different in each of the n repeating units, and salts thereof, (2) A method for production of the compounds (I) or salts thereof characterized in that a compound of the formula (II)

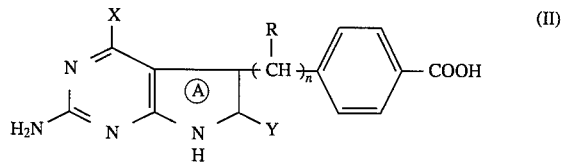

wherein the ring Ⓐ is a pyrrole or pyrroline ring, X is an amino group or a hydroxyl group, Y is a hydrogen atom, an amino group or a hydroxyl group, R is a hydrogen atom, a fluorine atom, an alkyl group, an alkenyl group or an alkynyl group, and n is an integer of 2 to 4, and R may be different in each of the n repeating units, a reactive derivative at the carboxyl group, or a salt thereof, and a compound of the formula (III)

wherein $-COOR^1$ and $-COOR^2$ are independently carboxyl groups which may be esterified, or a salt thereof, are allowed to react.

(3) A compound of the formula (IV)

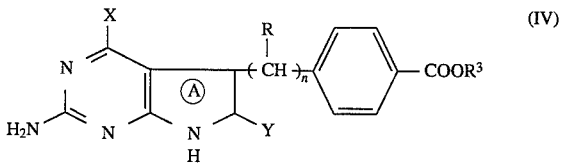

wherein the ring Ⓐ is a pyrrole or pyrroiine ring, X is an amino group or a hydroxyl group, Y is a hydrogen atom, an amino group or a hydroxyl group, R is a hydrogen atom, a fluorine atom, an alkyl group, an alkenyl group or an alkynyl group, $-COOR^3$ is a carboxyl group which may be esterified and n is an integer of 2 to 4, and R may be different in each of the n repeating units, and salts thereof.

(4) Anti-tumor agents containing the compounds (I) or salts thereof.

When X or Y in the formulas described above is a hydroxyl group, each of the compounds (I), (II) and (IV) may exist as an equilibrium mixture of the respective tautomers. The following partial structural formulas show the sites of the structure which are subject to tautomerism, and the equilibrium between the tautomers is illustrated in the following.

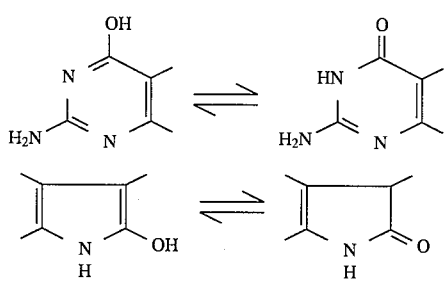

For the convenience of description, only the hydroxyl forms and the corresponding names are described throughout this specification, but the corresponding oxo forms are always included.

There may be two or more asymmetric centers in the compounds (I) of this intention, and the absolute configuration at all of the asyrmmetric carbon atoms may be the S, R or S-R mixed form, except that the absolute configuration at the asymmetric carbon atom in the side chain derived from glutamic acid is always S(L). Therefore the compounds (I) may have two or more diastereomers which, if necessary, can easily be separated from each other by a routine method for separation and purification. All of the diastereomers which can be separated by such a method are included in this invention.

Alkyl groups represented by R in the formulas described above include alkenyl groups having 1 to 3 carbon atom(s) each (e.g. methyl, ethyl, propyl, isopropyl groups). Alkenyl groups represented by R in the formulas described above include alkenyl groups having 2 to 3 carbon atom(s) each (e.g. vinyl, 1-methylvinyl, 1-propenyl, allyl, allenyl groups). Alkynyl groups represented by R in the formulas described above include alkynyl groups having 2 to 3 carbon atom(s) each (e.g. ethynyl, 1-propynyl, propagyl groups). Carboxyl groups in the carboxyl groups which may be esterified, represented by —COOR$^1$, —COOR$^2$ and —COOR$^3$ include carboxyl groups which may be esterified by alkyl groups having 1 to 5 carbon atom(s) each, benzyl groups which may be substituted or phenyl groups which may be substituted. The alkyl groups include methyl, ethyl, propyl, isopropyl, n-butyl, iso-butyl, sec-butyl, tert-butyl, n-pentyl, iso-pentyl, sec-pentyl, neo-pentyl and tert-pentyl. The benzyl groups which may be substituted include benzyl, nitrobenzyl, methoxybenzyl groups and so on. The phenyl groups which may be substituted include phenyl, nitrophenyl, methoxyphenyl groups and so on.

In the following the method for production of the compounds (I) of this invention is explained.

The compounds (I) can be obtained by acylation of glutamic acid derivatives shown by the formula (III) with carboxylic acids shown by the formula (II) or reactive derivatives thereof. The acylation may be performed, for example, by acylation of the compound (III) with the compound (II) in the presence of carbodiimide, dephenylphosphoryl azide or diethyl phosphoro cyanidate. Generally about 1 to 20 mole equivalent, preferably 1 to 5 mole equivalent of the compound (III) relative to the compound (II) is used. Generally about 1 to 25 mole equivalent, preferably about 1 to 5 mole equivalent of a carbodiimide relative to the compound (II) is used. As the carbodiimide, dicyclohexylcarbodiimide is preferable for practical use, but other carbodiimides such as diphenylcarbodiimide, di-o-tolylcarbodiimide, di-p-tolylcarbodiimide, di-tert-butylcarbodiimide, 1-cyclohexyl-3-(2-morpholinoehtyl)carbodiimide, 1-cyclohexyl-3-(4-diethylaminocyclohexyl)carbodiimide, 1-ethyl-3-(2-diethylaminopropyl)carbodiimide and 1-ethyl-3-(3-diethylaminopropyl)carbodiimide may be used. The acylation is preferably performed in the presence of a suitable solvent, and such solvents include water, alcohols (e.g. methanol, ethanol, etc.), ethers (e.g. dimethyl ether, diethyl ether, tetrahydrofuran, dioxane, monogtyme, diglyme, etc.), nitriles (e.g. acetonitrile, etc.), esters (e.g. ethyl acetate, etc.), halogenated hydrocarbons (e.g. dichloromethane, chloroform, carbon tetrachloride, etc.), aromatic hydrocarbons (e.g. benzene, toluene, xylene, etc.), acetone, nitromethane, pyridine, dimethylsulfoxide, dimethylformamide, hexamethylphospholamide, sulfolane, and the suitable mixtures of two or more of these solvents. The reaction is allowed to proceed generally at a pH ranging from 2 to 14, preferably at a pH ranging from about 6 to 9, at a temperature ranging from about −10° C. to the boiling point of the solvent used (up to about 100° C.), preferably at a temperature ranging from about 0° to 50° C., for about 1 to 100 hours. The pH of the reaction mixture is adjusted, if necessary, by addition of an acid (e.g. hydrochloric acid, sulfuric acid, phosphoric acid, nitric acid, acetic acid, etc.), a base (e.g. sodium alcoholate such as sodium methylate and sodium ethylate, hydroxides of alkali metals or of alkali earth metals such as sodium hydroxide, potassium hydroxide, lithium hydroxide, barium hydroxide, carbonates or bicarbonates of alkali metals or of alkali earth metals such as sodium carbonate, potassium carbonate, barium carbonate, calcium carbonate and sodium biccarbonate, amines such as trimethylamine, triethylamine, triethanolamine and pyridine), or a buffer (e.g. phosphate buffer, borate buffer, acetate buffer, etc.). The reaction can proceed more advantageously in the presence of a catalyst which promotes acylation. Such catylysts include base catalysts and acid catalysts. The base catalysts include tertiary amines (e.g. aliphatic tertiary amines such as triethylamine; aromatic tertiary amines such as pyridine, α-, β- or γ-picoline, 2,6-lutidine, 4-dimethylaminopyridine, 4-(1-pyrrolidinyl)pyridine, dimethylaniline and diethylaniline), and such acid catalysts include Lewis acids [e.g. anhydrous zinc chloride, anhydrous aluminum chloride (AlCl$_3$), anhydrous ferric chloride, titanium tetrachloride (TiCl$_4$), tin tetrachloride (SnCl$_4$), antimony pentachloride, cobalt chloride, cupric chloride, boron trifluoride ethyl ether complex, etc.]. Among the catalysts described above, 4-dimethylaminopyridine or 4-(1-pyrrolidinyl)pyridine is preferable in many cases. The suitable amount of the catalyst is such that is enough to oromote the acylation being generally about 0. 01 to 10 mole equivalent, preferably about 0.1 to 1 mole equivalent relative to the compound (II). The reactive derivatives of carboxylic acids obtained by the reaction at the carboxyl group, used for the acylation include acid halides (e.g. fluoride, chloride, bromide, iodide), acid anhydrides (e.g. iodoacetic acid anhydride, isobutyric acid anhydride), mixed acid anhydrides with monoalkylcarbonic acid esters (e.g. mono-methylcarbonic acid ester, monoethylcarbonic acid ester, monopropylcarbonic ester, mono-iso-propylcarbonic acid ester, monobutylcarbonic acid ester, mono-iso-butylcarbonic acid ester, mono-sec-butylcarbonic acid ester, mono-tert-butylcarbonic acid ester), active esters (e.g. cyanomethyl ester, carboethoxymethyl ester, methoxymethyl ester, phenyl ester, o-nitrophenyl ester, p-nitrophenyl ester, p-carbomethoxyphenyl ester, p-cyanophenyl ester, thiophenyl ester), acid azidest mixed acid anhydrides with phosphoric acid diesters (e.g. dimethyl phosphate, diethyl phosphate, dibenzylphosphate, diphenylphosphate), and mixed acid anhydrides with phosphorous acid diesters (e.g. dimethyl phosphite, diethyl phosphite, dibenzyl phosphite, diphenyl phosphite), of the carboxylic acid (II). For acylation with such a reactive derivative, the solvent, the catalyst and the reaction temperature are the same as for acylation in the presence of the carbodiimide described above.

For production of the compound (I-1) in which —COOR$^1$ and —COOR$^2$ in the formula of the compound (I) are carboxyl groups, it is desirable that the compound in which —COOR$^1$ and —COOR$^2$ in the formula of the compound (III) are esterified carboxyl groups is allowed to react with the compound (II) followed by deesterification by per se known degradation or catalytic reduction. Such degradation can be performed by hydrolysis under basic conditions (method A), hydrolysis under acidic conditions (method B-1) or hydrolysis under acidic nonaqueous conditions (method B-2). Bases used in the method A include metal alkoxides such as sodium methoxide, sodium ethoxide, sodium butoxide and potassium butoxide, metal hydroxides such as sodium hydroxide, potassium hydroxide, lithium hydroxide and barium hydroxide, and amines such as ammonia, triethylamine and pyridine. Acids used in the method B-1 include mineral acids such as hydrochloric acid, hydrobromic acid, sulfuric acid, nitric acid and phosphoric acid, and organic acids such as trifluoroacetic acid, trichloroacetic acid, methanesulfonic acid, benzenesulfonic acid, p-toluenesulfonic acid and camphorsulfonic acid. Catalysts used in the method B-2 include mineral acids such as hydrogen chloride, hydrogen bromide, perchloric acid, sulfuric acid, nitric acid and phosphoric acid, organic acids such as trifluoroacetic acid, trichloroacetic acid, methanesulfonic acid, benzenesulfonic acid, p-toluenesulfonic acid and camphorsulfonic acid, and Lewis acids such as anhydrous zinc chloride, anhydrous aluminum chloride (AlCl$_3$), anhydrous ferric chloride, titanium tetrachloride (TiCl$_4$), tin tetrachloride (SnCl$_4$), antimony pentachloride, cobalt chloride, cuprio chloride and boron trifuluoride ethyl ether complex. Degradation is performed in a suitable solvent at a temperature ranging from 0° C. to the boiling point of the solvent, preferably at 10° to 80° C. for 30 minutes to 2 days. The solvent used for the reaction by the method A or by the method B-1 may be water, methanol, ethanol, propanol, butanol, ethyleneglycol, methoxyethanol, ethoxyethanol, tetrahydrofuran, dioxane, monoglyme, diglyme, pyridine, dimethylformamide, dimethylsulfoxide or sulfolane, or a suitable mixture of two or more of these solvents; the solvent used for the reaction by the method B-2 may be ethyl acetate, dimetyl ether, diethyl ether, tetrahydrofuan, dioxane, monogtyme, diglyme, dichloromethane, chloroform, carbon tetrachloride, acetonitrile, benzene, toluene, xylene, nitromethane or pyridine, or a suitable mixture of two or more of these solvents. The catalytic reduction (method C) is performed in a suitable solvent at a temperature ranging from about –40° C. to the boiling point of the solvent used, preferably at about 0° to 50° C. The solvents used include water., alcohols (e.g. methanol, ethanol, propanol, iso-propanol, butylalcohol, sec-butylalcohol, tert-butylalcohol, ethyleneglycol, methoxyethanol, ethoxyethanol), acetic acid esters (e.g. methyl acetate, ethyl acetate), ethers (e.g. dimethyl ether, diethyl ether, tetrahydrofuran, dioxane, monoglyme, diglyme, aromatic hydrocarbons (e.g. benzene, toluene, xylene), pyridine, dimethylformamide and suitable mixtures of two or more of these solvents. Catalysts for the catalytic reaction include palladium, platinum, rhodium and Raney nickel. Addition of a trace amount of acetic acid, trifluoroacetic acid, hydrochloric acid or sulfuric acid can allow the reaction to proceed advantageously.

The method for production of the compound (I-1) is selected according to the nature of —COOR$^1$ and —COOR$^2$; when —COOR$^1$ and —COOR$^2$ are carboxyl groups esterified with methyl, ethyl, propyl, butyl, sec-butyl, phenyl or substituted phenyl group, the method A or the method B-1 is applied advantageously; when —COOR$^1$ and —COOR$^2$ are carboxyl groups esterified with iso-propyl or tert-butyl group, the method B-2 is applied advantageously; and when —COOR$^1$ and —COOR$^2$ are carboxyl groups esterified with benzyl or a substituted benzyl group, the method B-1 or the method C is applied advantageously. When —COOR$^1$ and —COOR$^2$ are different from each other, the methods A, B-1, B-2 and C may be combined appropriately.

In the following the method for production of the starting compound (II) is explained.

The compound (II) wherein the ring Ⓐ is a pyrrole ring, can be produced, for example, by the following processes.

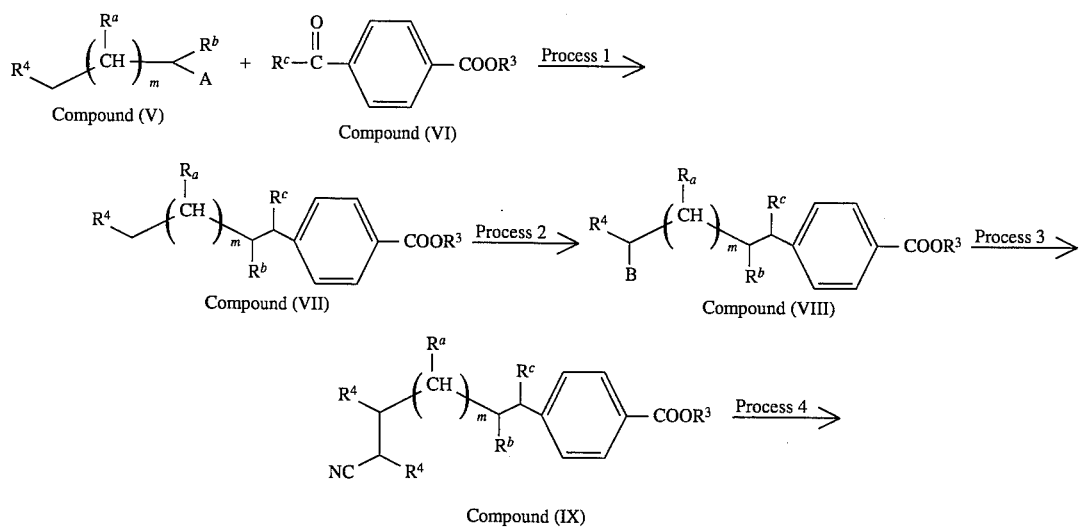

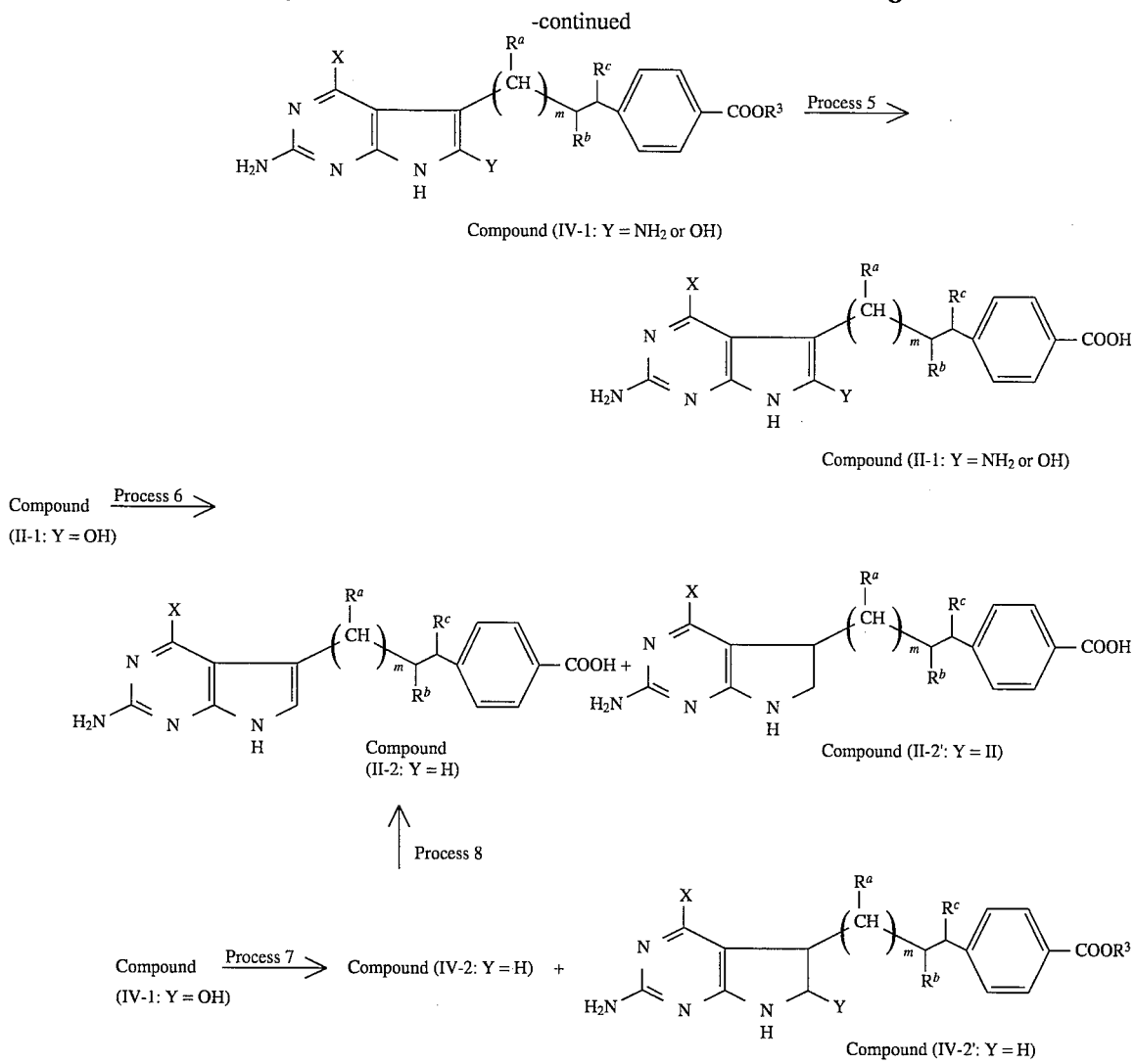

In the reaction formulas described above, X, Y and $R^3$ are the same as described before; $R^a$, $R^b$ and $R^c$ are independently a hydrogen atom, a fluorine atom or an alkyl group (the same as those represented by R described before); $R^4$ is a cyano group or an esterified carboxyl group represented by the formula —$COOR^6$; A is a hydrogen atom or a halogen atom (e.g. fluorine atom, chlorine atom, bromine atom, iodine atom); B is a halogen atom (e.g. chlorine atom, bromine atom, iodine atom) or an eliminable group which may be easily derived from hydroxy group (e.g. methanesulfonyloxy group, benzenesulfonyloxy group, p-toluenesulfonyloxy group, trifluoromethanesulfonyloxy group); and m is 0, 1 or 2. $R^6$ in the esterified carboxyl group represented by the formula —$COOR^6$ is exemplified by an alkyl group having 1 to 4 carbon atom(s) (e.g. methyl, ethyl, propyl, isopropyl, butyl, sec-butyl, tert-butyl, etc.), phenyl or substituted phenyl group (p-nitrophenyl, p-methoxyphenyl, etc.), and benzyl or substituted benzyl (e.g. p-nitrobenzyl, p-methoxybenzyl, etc.).

The compound (V) may be dehydrogenated on the possible position between the two adjacent carbons and form an unsaturated bond.

In the following the reaction processes described above are explained in detail.

Process 1

The compound (V) and the compound (VI) are subjected to condensation and the resulting product is subjected to reduction to give the compound (VII).

For the condensation, a known reaction (e.g. aldol reaction, Reformatsky reaction, Witrig reaction, etc.) is employable, and for the reduction, usually a catalytic reduction under hydrogen atmosphere in the presence of a catalyst (e.g. nickel, palladium, platinum, rhodium) is advantageously employed.

In the condensation by aldol reaction, the employable base catalysts include metal byrdoxides such as sodium hydroxide, potassium hydroxide, lithium hydroxide and barium hydroxide, metal alkoxides such as sodium methoxide, sodium ethoxide and potassium tert-butoxide, metal amides such as sodium amide and lithium diisopropylamide, metal hydrides such as sodium hydride and potassium hydride, organic metal compounds such as phenyllithium and butyllithium and amines such as triethylamine, pyridine, α-, β- or γ-picoline, 2,6-lutidine, 4-dimethylaminopyridine, 4-(1-pyrrolidinyl)pyridine, dimethylaniline and diethylaniline; the employable acid catalysts include mineral acids such as hydrochloric acid, sulfuric acid, nitric acid, phosphoric acid and boric acid, and organic acids such as oxalic acid, tartaric acid, acetic acid, trifluoroacetic acid, methanesulfonic acid, benzenesulfonic acid, p-toluenesulfonic acid and camphorsulfonic acid. The condensation can be conducted according to the known method [Ei-Ichi Negishi, Organometallics in Organic Synthesis, vol. 1, John Wiley & Sons, New York Chickester, Brisbane, Toronto (1980)] which comprises converting a ketone form into the silylenolether form which is then subjected to condensation with an aldehyde or an equivalent in the presence of a Lewis acid [e.g. anhydrous zinc chloride, anhydrous aluminum chloride ($AlCl_3$), anhydrous ferric chloride, titanium tetrachloride ($TiCl_4$), tin tetrachloride ($SnCl_4$), antimony pentachloride, cobalt chloride, cupric ghloride, boron trifluoride ethyl ether complex, etc.], or converting a ketone form into the enolate by treating the ketone form with a metal triflate (e.g. dialkyl boron tin (II) triflate) in the presence of amines (e.g. triethylamine, pyridine, α-, β- or γ-picoline, 2,6-lutidine, 4-dimethylaminopyridine, 4-(1-pyrrolidinyl)pyridine, dimethylaniline, diethylaniline) followed by subjecting the enolate to condensation with an aldehyde or an equivalent. The condensation is conducted in a suitable solvent at a temperature ranging from $-100°$ C. to the boiling point of the solvent, preferably ranging from $-78°$ to $100°$ C., for 1 minute to 3 days. Solvents employable for the reaction include water, liquid ammonia, alcohols (e.g. methanol, ethanol, propanol, isopropanol, butyl alcohol, sec-butyl alcohol, tert-butyl alcohol, ethylene glycol, methoxyethanol, ethoxyethanol), ethers (e.g. dimethyl ether, diethyl ether, tetrahydrofuran, dioxane, monoglyme, diglyme), halogenated hydrocarbons (e.g. dichloromethane, chloroform, carbon tetrachloride), aliphatic hydrocarbons (e.g. pentane, hexane, heptane), aromatic hydrocarbons (e.g. benzene, toluene, xylene), dimethylformamide, dimethylsulfoxide, hexamethylphospholamide, sulfolane, and the suitable mixtures thereof. In the condensation by Wittig reaction, the employable reagents include metal hydroxides such as sodium hydroxide, potassium hydroxide, lithium hydroxide and barium hydroxide, metal alkoxides such as sodium meshoxide, sodium ethoxide and potassium tert-butoxide, metal amides such as sodium amide and lithium diisopropylamide, metal hydrides such as sodium hydride and potassium hydride, organic metal compounds such as phenyllithium and butyllithium, and amines such as triethylamine, pyridine, α-, β-, or γ-picoline, 2,6-1utidine, 4-dimethylaminopyridine, 4-(1-pyrrolidinyl)pyridine, dimethylaniline and diethylaniline. The reaction is conducted in a suitable solvent at a temperature ranging from $-20°$ C. to the boiling point of the solvent used, preferably ranging from $0°$ to $150°$ C., for 1 minute to 10 days. The solvents employable for the reaction include liquid ammonia, alcohols (e.g. methanol, ethanol, propanol, isopropanol, butyl alcohol, sec-butyl alcohol, tert-buty1 alcohol, ethylene glycol, mehoxyethanol, ethoxyethanol), ethers (e.g. dimethyl ether, diethyl ether, tetrahydrofuran, dioxane, monoglyme, diglyme, aliphatic hydrocarbons (e.g. pentane, hexane, heptane), aromatic hydrocarbons (e.g. benzene, toluene, xylene), dimethylformamide, dimethylsulfoxide, hexamethylphospholamide, sulfolane and the suitable mixtures thereof.

The condensation can also be conducted by using a Reformatsky reaction. The reagents employable for the Reformatsky reaction include zinc, magnesium, aluminum and tin, and the reaction is conducted in a suitable solvent at a temperature ranging from $-20°$ C. to the boiling point of the solvent used, preferably ranging from $0°$ to $150°$ C., for 30 minutes to 3 days. The solvents employable for the reaction include ethers (e.g. dimethyl ether, diethyl ether, tetrahydrofuran, dioxane, monoglyme, diglyme), aliphatic hydrocarbons (e.g. pentane, hexane, heptane), aromatic hydrocarbons (e.g. benzene, toluene, xylene) and the suitable mixtures thereof.

The reaction conditions for the catalytic reduction are the same as those for the deesterification at the $—COOR^1$ and $—COOR^2$ of the compound (III) (method C).

The starting materials (V) and (VI) can be obtained easily according to the known methods described in the literature. [B. Neises et al., Angew. Chem. Int. Ed. Engl., 17, 522 (1978)].

Process 2

This is the process whereby an eliminable functional group B is introduced into the active methylene (the α-position of the carbonic acid ester) of the compound (VIII): it can be conducted easily by using known reagents according to a per se known method.

Process 3

The compound (VIII) obtained in the Process 2 is subjected to condensation with matononitrile or a cyanoacetic acid ester [$NC—CH_2COOR^6$; $R^6$ is the same as described above] under a basic condition, to give the compound (IX). The employable bases, solvents and reaction conditions are in accordance with the known methods.

Process 4

The compound (IX), when treated with guanidine, can react at the cyano group or the ester residue followed by ring closure to form newly a pyrrolopyrimidine ring. Ring closure under a basic condition allows the reaction to proceed advantageously. The employable bases include metal alkoxides such as sodium mothoxide, sodium ethoxide and potassium tert-butoxide. The employable solvents for the reaction include methanol, ethanol, propanol, tert-butyl alcohol, dimethylsulfoxide and hexamethylphospholamide. The reaction temperature ranges from $0°$ to $150°$ C., preferably from $20°$ to $100°$ C. The reaction time ranges from 1 to 48 hours.

Process 5

The compound (IV-1: $Y=NH_2$ or OH) obtained in the Process 4 can be converted into the compound (II-1: $Y=NH_2$ or OH) by subjecting the ester residue [$—COOR^3$] to the deesterification used in the preparation of the compound Process 6

The compound (II-1: Y=OH) obtained in the Process 5 is subjected to reduction to give the compound (II-2): Y=H). The conditions for the reduction are per se known, and reduction by a metal hydride (e.g. borane, alane or ate complexes thereof) is employed advantageously.

The Process 5 and the Process 6 may be conducted in the reverse order. Namely, in the Process 7 the compound (IV-1: Y=OH) is subjected to reduction similar to that in the Process 6 to give the compound (IV-2: Y=H), which is then subjected to deesterification in the Process 8 in a similar manner as in the Process 5 to give the compound (II-2: Y=H). Either the deesterification or the reduction can be selected to be conducted in advance to the other according to the nature of the substituents in the compound (IV-1: Y=OH).

In the above Processes 6 and 8, the mixture containing the compounds (II-2) and (II-2') or the compounds (IV-2) and (IV-2') may be separated, or each of the compounds (II-2) and (II-2') or each of the compounds (IV-2) and (IV-2') is synthesized predominantly by selective reduction.

Among the compounds those represented by the formula (II-3: X=OH)

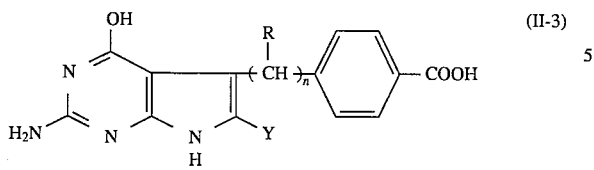

wherein R and n mean the same as described before, can be obtained also by the following processes.

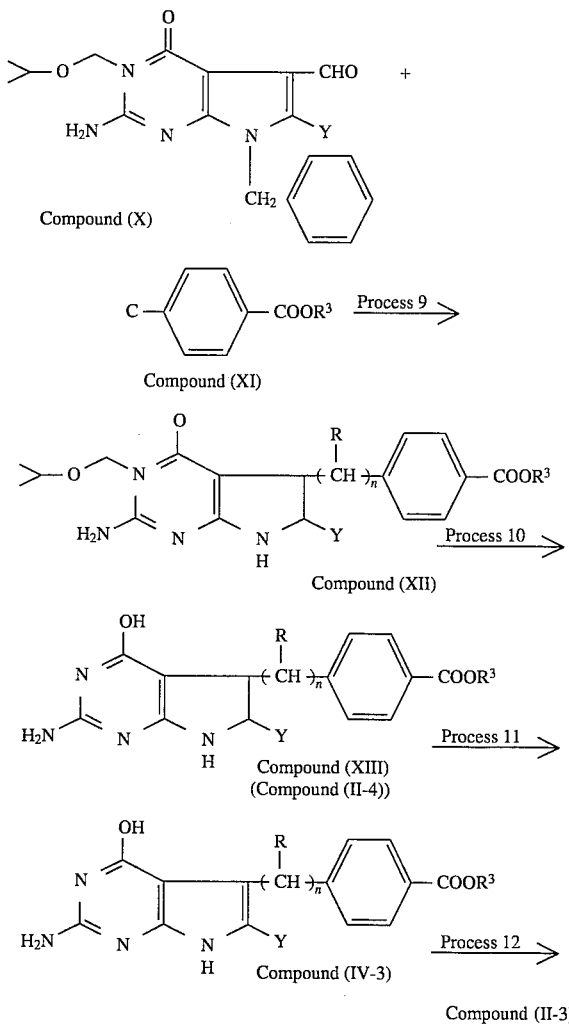

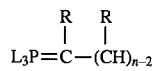

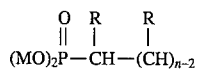

In the Processes described-above, R, Ra, Y and n mean the same as described before and Z means the formula RCH$_2$CO— wherein R means the same as described above, the formula $$L_3P=\underset{\underset{R}{|}}{C}-(CH)_{n-2}\underset{\underset{R}{|}}{}$$

wherein L is phenyl, butyl or cyclohexyl, and R and n mean the same as described above, or the formula $$(MO)_2\underset{\underset{O}{\|}}{P}-\underset{\underset{R}{|}}{CH}-(CH)_{n-2}\underset{\underset{R}{|}}{}$$

wherein M is ethyl or phenyl, and R and n mean the same as described above. It is preferable that Y is hydrogen.

In the following these Processes are explained.

Process 9

The compound (X) [T. Kondo et al., Chemistry Letters, 419 (1983)] and a para-substituted benzoic acid ester derivative (XI) are subjected to condensation (aldo reaction, Wittig reaction) followed by catalytic reduction under hydrogen atmosphere, to give the compound (XII). For the condensation are applicable the reaction conditions, the reaction solvents, the reaction temperatures and the reagents used in the Process I. For the catalytic reduction under hydrogen atmosphere are applicable the conditions used in the deesterification of —COOR$^1$ and —COOR$^2$ of the compound (III).

Process 10

Treatment of the compound (XII) under acidic conditions can eliminate the protection of the isopropyloxymethyl group at the 3-position to give the compound (XIII). The conditions, solvents and temperatures used in deesterification of —COOR$^1$ and —COOR$^2$ of the compound (III) (the method B-1 and the method B-2) are employable for the reaction.

Process 11

The compound (XIII) obtained in the Process 10 is subjected to dehydrogenation by a per se known method, to be easily converted into the compound (IV-3: Y=H).

Process 12

The compound (IV-3: Y=H) obtained in the Process 11 can be converted into the compound (II-3) by deesterification. The conditions, solvents and temperatures described in detail for the deesterification of —COOR$^1$ and —COOR$^2$ of the compound (III) (the methods A, B-1, B-2 and C) are employable for the reaction. The processes 10 to 12 may be conducted in any order with the formation of the respective products, and finally the desired compound (II-3) is obtained. The order is determined suitably according to the nature of the substituents of the compounds (XII), (XIII) and (IV-3). The compound (II-3) thus obtained can be converted, if necessary, into the compound (II-2) by a known substituent-converting reaction on the pyrimidine ring reported in the literature. [Protein Nucleic acid Enzyme Extra issue, Chemical synthesis of nucteic acids, Kyoritsu Shuppan (1968)].

The compounds other than the compound (II-3), wherein X is hydroxyl can be also converted into the corresponding compounds wherein X is amino by the above-mentioned substituent-converting reaction.

The reactions, reagents and reaction conditions used in the Processes 1 to 12 and in the production of the starting compounds (V) and (XIII) are known and explained in detail in the following literature. [J. F. W. Mcomine, Protective Groups in Organic Chemistry, Plenum Press, London and New York (1973)], [Pine, Hendrikson, Hammond, Organic Chemistry (4th edition) [I]-[II], Hirokawa Shoten (1982)], and [M. Fieser and L. Fieser, Reagents for Organic Synthesis vol. 1–10, Wiley-Interscience, New York, London, Sydney and Toronto (1969–1982)].

The intermediates of the compounds of this invention and the compounds (I) of this invention can be isolated from the reaction mixtures by the conventional means for separation and purification, such as concentration, extraction with solvent, chromatography and recrystallization.

The compounds (I), (II) and (IV) of this invention may form salts. Such salts are produced by the known methods, and exemplified by the salts of pharmaceutically acceptable bases or acids and quaternary salts. Salts of bases include salts of alkali metals, alkali earth metals, non-toxic metals, ammonium and substituted ammonium, such as sodium, potassium, lithium, calcium, magnesium, aluminum, zinc, ammonium, trimethylammonium, triethylammonium, triethanolammonium, pyridinium and substituted pyridinium. Salts of acids include salts of mineral acids such as hydrochloric acid, sulfuric acid, nitric acid, phosphoric acid and boric acid, and salts of organic acids such as oxalic acid, tartaric acid, acetic acid, trifluoroacetic acid, methanesulfonic acid and camphorsulfonic acid. Quaternary salts include salts of methyl bromide, methyl iodide, methyl methanesulfonate, methyl benzensulfonate and methyl p-toluenesulfonate. Also, the compounds (I), (II) and (IV) may form zwitterion.

As the compounds (I) of this invention, the following compounds are exemplified:

Diethyl N-[4-[3-(2,4-diamino-7H-pyrrolo[2,3-d]-pyrimidin-5-yl)propyl]benzoyl]-L-glutamate,
N-[4-[3-(2,4-diamino-7H-pyrrolo[2,3-d]pyrimidin-5-yl-)propyl]benzoyl]-L-glutamic acid,
Diethyl N-[4-[3-(2,4-diamino-6-hydroxy-7H-pyrrolo[2,3-d]pyrimidin-5yl)propyl]benzoyl]-L-glutamate,
N-[4-[3-(2,4-diamino-6-hydroxy-7H-pyrrolo[2,3-d]-pyrimidin-5-yl)propyl]benzoyl]-L-glutamic acid,
Diethyl N-[4-[3-(2-amino-4-hydroxy-7H-pyrrolo[2,3-d]pyrimidin-5yl)propy benzoyl]-L-glutamate,
N-[4-[3-(2-amino-4-hydroxy-7H-pyrrolo[2,3-d]pyrimidin-5-yl)propyl]benzoyl]-L-glutamic acid,
Diethyl N-[4-[3-(2-amino-4-hydroxy-5,6-dihydropyrrolo[2,3-d]pyrimidin 5-yl)propyl]benzoyl]-L-glutamate,
Diethyl N-[4-[2-(2-amino-4-hydroxy-5,6-dihydropyrrolo[2,3-d]pyrimidin-5-yl)ethyl]benzoyl]-L-glutamate,
Diethyl N-[4-[3-(2,4-diamino-5,6-dihydropyrrolo[2,3-d]pyrimidin-5-yl)propyl]benzoyl]-L-glutamate,
N-[4-[3-(2-amino-4-hydroxy-5,6-dihydropyrrolo[2,3-d]pyrimidin-5-yl)propyl]benzoyl]-L-glutamic acid,
N-[4-[2-(2-amino-4-hydroxy-5,6-dihydropyrrolo[2,3-d]pyrimidin-5-yl)ethyl]benzoyl]-L-glutamic acid,
N-[4-[3-(2,4-diamino-5,6-dihydropyrrolo[2,3-d]pyrimidin-5-yl) propyl]benzoyl]-L-glutamic acid,
Diethyl N-[4-[3-(2,4-diamino-6,7-dihydro-5H-pyrrolo[2,3-d]pyrimidin-5-yl)-1-methylpropyl]benzoyl]-L-glutamate,
N-[4-[3-(2,4-diamino-6,7-dihydro-5H-pyrrolo[2,3-d]pyrimidin-5-yl)-1-methylpropyl]benzoyl]-L-glutamic acid,
Diethyl N-[4-[3-(2,4-diamino-7H-pyrrolo[2,3-d]pyrimidin-5-yl)-1-methylpropyl]benzoyl]-L-glutamic acid,
N-[4-[3-(2,4-diamino-7H-pyrrolo[2,3-d]pyrimidin-5-yl)-1-methylpropyl]benzoyl]-L-glutamic acid,
N-[4-[3-(2,4-diamino-7H-pyrrolo[2,3-d]pyrimidin-5-yl)-methyl-propyl]benzoyl]-L-glutamic acid,
N-[4-[3-(2,4-diamino-7H-pyrrolo[2,3-d]pyrimidin-5-yl)-1-ethylpropyl]benzoyl]-L-glutamic acid,
N-[4-[3-(2,4-diamino-7H-pyrro[2,3-d]pyrimidin-5-yl)-5]-ethylpropyl]benzoyl]-L-glutamic acid,
N-[4-[3-(2,4-diamino-7H-pyrro[2,3-d]pyrimidin-5-yl)-1vinylpropyl]benzoyl]-L-glutamic acid,
N-[4-[3-(2,4-diamino-7H-pyrro[2,3-d]pyrimidin-5yl)-2-vinylpropyl]benzoyl]-L-glutamic acid,
N-[4-[3-(2,4-diamino-7H-pyrro[2,3-d]pyrimidin-5-yl)-1-allylpropyl]benzoyl]-L-glutamic acid,
N-[4-[3-(2,4-diamino-7H-pyrro[2,3-d]pyrimidin-5-yl)-2-allylpropyt]benzoyl]-L-glutamic acid,
N-[4-[3-(2,4-diamino-7H-pyrro[2,3-d]pyrimidin-5-yl)-(propen-1-yl)propyl]benzoyl-L-glutamic acid,
N-[4-[3-(2,4-diamino-7H-pyrro[2,3-d]pyrimidin-5-yl)-(propen-1-yl)-propyl]benzoyl]-L-glutamic acid,
N-[4-[3-(2,4-diamino-7H-pyrro[2,3-d]pyrimidin-5-yl)-1-ethynylpropyl]benzoyl]-L-glutamic acid,
N-[4-[3-(2,4-diamino-7H-pyrro[2,3-d]pyrimidin-5-yl)-2ethynylpropyl]benzoyl]-L-glutamic acid,
N-[4-[3-(2,4-diamino-7H-pyrro[2,3-d]pyrimidin-5-yl)-1-propagylpropyl]benzoyl-L-glutamic acid,
N-[4-[3-(2,4-diamino-7H-pyrro[2,3-d]pyrimidin-5-yl)-2-propagylpropyl]benzoyl]-L-glutamic acid,
N-[4-[3-(2,4-diamino-7H-pyrro[2,3-d]pyrimidin-5-yl)-1-(propyn-1-propyl]benzoyl]-L-glutamic acid,
N-[4-[3-(2,4-diamino-7H-pyrro[2,3-d]pyrimidin-5-yl)-1-(propyn-1-yl)propyl]benzoyl]-L-glutamic acid,
N-[4-[3-(2,4-diamino-7H-pyrro[2,3-d]pyrimidin-5-yl)-2-(propyn-1-yl)-propyl]benzoyl]-L-glutamic acid,
N-[4-[3-(2,4-diamino-6,7-dihydro-5H-pyrro[2,3-d]pyrimidin-5-yl)-2-methylpropyl]benzoyl]-L-glutamic acid,
N-[4-[3-(2,4-diamino-6,7-dihydro-5H-pyrro[2,3-d]N-[4-[3-(2,4-diamino-6,7-dihydro-5H-pyrro[2,3-d]pyrimidin-5-yl)-1-ethylpropyl]benzoyl]-L-glutamtic acid,
N-[4-[3-(2,4-diamino-6,7-dihydro-5H-pyrro[2,3-d]pyrimidin-5-yl)-2-ethylpropyl]benzoyl]-L-glutamic acid,
N-[4-[3-(2,4-diamino-6,7-dihydro-5H-pyrro[2,3-d]pyrimidin-5-yl)-1-vinylpropyl]benzoyl]-L-glutamic acid,
N-[4-[3-(2,4-diamino-6,7-dihydro-5H-pyrro[2,3-]pyrimidin-5-yl)-2-vinylpropyl]benzoyl]-L-glutamatic acid,
N-[4-[3-(2,4-diamino-6,7-dihydro-5H-pyrro[2,3-d]pyrimidin-5-yl)-1-allylpropyl]benzoyl]-L-glutamic acid,
N-[4-[3-(2,4-diamino-6,7-dihydro-5H-pyrro[2,3-d]pyrimidin-5-yl)-2-allylpropyl]benzoyl]-L-glutamatic acid,
N-[4-[3-(2,4-diamino-6,7-dihydro-5H-pyrro[2,3-d]pyrimidin-5-yl)-1-(propen-1-yl]benzoyl]-L-glutamic acid,
N-[4-[3-(2,4-diamino-6,7-dihydro-5H-pyrro[2,3-d]pyrimidin-5-yl)-2-(propen-1-yl]propyl]benzoyl]-L-glutamic acid,
N-[4-[3-(2,4-diamino-6,7-dihydro-5H-pyrro[2,3-d]pyrimidin-5-yl)-1-ethylpropyl]benzoyl]-L-glutamic acid,
N-[4-[3-(2,4-diamino-6,7-dihydro-5H-pyrro[2,3-d]pyrimidin-5-yl)-2-ethylpropyl]benzoyl]-L-glutamic acid,
N-[4-[3-(2,4-diamino-6,7-dihydro-5H-pyrro[2,3-d]pyrimidin-5-yl)-1-propagylpropyl]benzoyl]-L-glutamic acid,
N-[4-[3-(2,4-diamino-6,7-dihydro-5H-pyrro[2,3-d]pyrimidin-5-yl)-2-propagylpropyl]benzoyl]-L-glutamic acid,
N-[4-[3-(2,4-diamino-6,7-dihydro-5H-pyrro[2,3-d]pyrimidin-5-yl)-1-(propyn-1-yl)propyl]benzoyl]-L-glutamic acid,
N-[4-[3-(2,4-diamino-6,7-dihydro-5H-pyrro[2,3-d]pyrimidin-5-yl)-2-(propyn-1-yl)propyl]benzoyl]-L-glutamic acid.

Effects

The compounds (I) of this invention show excellent antitumor effects in mouse tumor cell strains (P388, L1210, L5178Y, B16 melanoma, MethA, Lewis Lung Carcinoma, S180 sarcoma, Ehrlich Carcinoma, Colon38) and human tumor cell strains (HL60, KB, Lu65), decrease the tumors carried by warm-blooded animals [e.g. melanoma, sarcoma, mastocytoma, carcinoma, neoptasia, etc.] and prolong the life-span of tumor-carrying warm-blooded animals.

In the following are described the results indicating the pharmaceutical effects of the compounds (I) of this invention.

The cell growth inhibiting effect ($IC_{50}$) of the compounds obtained in the Workina Examples described below in KB cells was determined by the following method.

Human nasopharyngeal cancer KB cells ($1 \times 10^4$ cells/ml) prepared according to a conventional method were inoculated into each well of the 96-microwell plate (0.1 ml in a well) and subjected to standing culture at 37° C. under 5% $CO_2$ for 24 hours. To this was added a solution of one of the compounds obtained in the Working Examples in 10%

MEM (Nissui Pharmaceutical Co. Ltd.), and subjected again to standing culture at 37° C. under 5% $CO_2$ for 72 hours. Then the culture was piperted out, and another 0.1 ml of the solution of MTT (Dojindo Laboratories) in 10% MEM (1.0 mg/ml) was added and incubated at 37° C. for 4 hours. Then 0.1 ml of the 10% SDS solution (Wako Pure Chemicals) was added and incubated at 37° C. for further 24 hours. The absorbance at 590 nm was measured and the $IC_{50}$ value of the compound was defined as the concentration of the compound required to decrease the number of cells in the untreated control group by 50%. The results obtained are shown in Table 1.

TABLE 1

| Test compound | $IC_{50}$ (µg/ml) |
| --- | --- |
| Compound of Working Example 4 | 0.0003 |
| Compound of Working Example 6 | 0.08 |
| Compound of Working Example 16 | 0.0006 |

In addition, the following are described the results indicating the pharmaceutical effects of the compounds (I) of this invention.

The cell growth inhibiting effect ($IC_{50}$) of the compound obtained in the Working Example 14 described below in HL-60 and HEL cells was determined by the following method.

(1) Human Leukemia cells HL-60 ($2 \times 10^5$ cetls/ml) were suspended in the GIT culture medium (Wako Pure Chemicals) containing the compound of this invention and 0.2 ml of the suspension was inoculated into each well of the 96-microwell plate. After standing culture at 37° C. under 5% $CO_2$ for 68 hours, 1 µCi of [$^3$H]-thymidine (5 Ci/mmol) was added and the mixture was incubated for 4 further hours. For measurement of the incorporation of thymidine into the cells, the acid-insoluble fraction was collected on a glass filter, and the radioactivity of the fraction was measured by a liquid scintillation counter. The $IC_{50}$ value of the compound was defined as the concentration of the compound required to decrease the radioactivity incorporated into the cells in the untreated control group by 50%.

(2) Human fetal normal lung fibroblasts HEL ($1 \times 10^4$ cells/ml) were suspended in the MEM culture medium (Nippon Flow Laboratories) and 0.1 ml of the suspension was inoculated into each well of the 96-microwell plate. After standing culture at 37° C. under 5% $CO_2$ for 24 hours, MEM culture medium containing the compound of this invention was added and the mixture was incubated for further 72 hours. The medium was replaced by the medium containing 1 µg/ml of MTT (Dojindo Laboratories), to which was added 10% SDS (Wako Pure Chemicals), and incubated overnight. Absorbance at 590 nm was measured by he Multiscan (Titertec Co.). The $IC_{50}$ value was determined by comparing the absorbance in the untreated contrel group. The results obtained are shown in Table 2.

TABLE 2

| Test compound | HL-60 (µg/ml) | HEL (µg/ml) |
| --- | --- | --- |
| Compound of Working Example 14 | 0.04 | >20.0 |

As shown by the above-mentioned results, the compounds (I) are excellent in inhibition of cell growth of KB and HL-60, while they do not exert a toxicity against HEL. The compounds (I) of this invention and the salts thereof are of low-toxicity, having remarkable antitumor effect. Therefore, the preparations containing the compound (I) or salts thereof can be employed as antitumor agents for the treatment of tumors in warm-blooded animals, particularly mammals (e.g. mouse, rat, cat,, dog, rabbit, etc.).

The compounds (I) and salts thereof, when used as antitumor agents, can be administered orally and parenterally as they are or in the forms of powders, granules, tablets, capsules, suppositories and injections, which are prepared according to the conventional methods using pharmaceutically acceptable excipients, vehicles, and diluents. The dose varies according to the animals, diseases, symptoms, compounds and administration routes; for example, the daily dose is about 2.0 to 100 mg of a compound of this invention per kg of body weight of a warm-blooded animal described above for oral administration, and about 1.0 to 50 mg/kg for parenteral administration. Injections may be administered intramuscularly, intraperitoneally, subsutaneously or intravenously.

The preparations are produced by the per se known processes. For the above-mentioned oral preparations, for example, tablets are produced by suitable combination with a binder (e.g. hydroxypropylcellulose, hydroxypropytmethylcellulose, macrogol, etc.), a disintegrator (e.g. starch, calcium carboxylmethylcellulose, etc.) and a lubricant (e.g. magnesium stearate, talc, etc.).

As parenteral preparations, for example, injections are produced by suitable combination with an agent to provide isotonicity (e.g. glucose, D-sorbitol, D-mannitol, sodium chloride, etc.), an antiseptic (e.g. benzyt alcohol, chlorobutanol, methyl p-hyrdoxybenzoate, propyl p-hydroxybenzoate, etc.) and a buffer (e.g. phosphate buffer, sodium acetate buffer, etc.).

An example process for production of tablets comprises mixing about 1.0 to 25 mg of the compound of this invention, 100 to 500 mg of lactose, about 50 to 100 mg of corn starch and about 5 to 20 mg of hydroxypropylcellulose for preparation of a tablet by a conventional means, granulating, mixing with corn starch and magnesium stearate and tabletting, so that tablets each weighing about 100 to 500 mg with the diameter of about 3 to 10 mm are obtained. The tablets may be coated with a mixture of acetone and ethanol, the mixture containing hydroxypropylmethylceilulose phthalate (about 10 to 20 mg per tablet) and castor oil (0.5 to 2 mg) at a concentration of about 5 to 10%, to give enteric coated tablets.

An example process for injectable preparation comprises dissolving about 2.0 to 50 mg of a sodium salt of the compound of this invention in about 2 ml of physiological saline for preparation of an ampoule, sealing the resultant solution in an ampoule and sterilizing the ampoule at 110° C. for about 30 minutes or adding about 2 ml of sterile distilled water containing about 10 to 40 mg of mannitol or sorbitol into the ampoule, freeze-drying and sealing the ampoule. For use of the freeze-dried comoound for subcutaneous, intravneous or intramuscular injection, the ampoule is opened and the content is dissolved in, for example, physioloaical saline so that the concentration of the compound may be about 1.0 to 25 mg/ml.

The following Reference Examples and Working Examples will explain the present invention more concretely.

Reference Example 1

Production of methyl 5-[4-(tert-butoxycarbonyl)phenyl] pentanoate:

Under an atmosphere of argon, potassium (25 g) was added to dried tert-butyl alcohol (820 ml), which was refluxed by heating to be dissolved completely. The solution was cooled to 20° C., to which ether (300 ml) was added and then a solution of methyl crotonate (63.93 g) and tert-butyl 4-formylbenzoate (71.0 g) in tert-butyl alcohol-ether (2:1, 300 ml) was added slowly while the inner temperature was kept at 10° C. After stirring at the same temperature for 2 hours, 1N potassium hydrogen sulfate in water (750 ml) was added with cooling so that the pH was adjusted to 4. The solution was extracted with ether, washed with water and then with saturated sodium chloride solution and subjected to evaporation of the solvent under reduced pressure. The resultant residue was dissolved in ethyl acetate (100 ml), to which 5%Pd-C (15 g: Engelhard Co. Ltd.) was added and stirred vigorously under hydrogen pressure of 4 kg/cm$^2$ at room temperature for 3 hours. The catalyst was filtered off, the solvent was evaporated under reduced pressure, to the residue were added dried methanol (200 ml), 4-(N,N-dimethylamino)pyridine (30 mg) and dichloromethane (250 ml), and then a solution of 1,3-dicyclohexylcarbodiimide (132 g) in dichloromethane (250 ml) was slowly added dropwise at 0° C. After stirring at room temperature for 18 hours, the mixture was cooled to 0° C.; which acetic acid (30 ml) was added and the mixture was stirred at 0° C. for 30 minutes and then at room temperature for 30 minutes. The resultant precipitate was filtrated off, the filtrate was concentrated to dryness under reduced pressure, to the residue was added ethyl acetate (100 ml) and after keeping at 0° C. for 2 hours, the resultant precipitate was again filtrated off. The filtrate was concentrated under reduced pressure and the residue was purified by column chromatography (carrier; silica gel, 100 g, developing solvent; ether: hexane=1:15→1:5), to give the object compound (59.7 g). melting point (Bp) 145°–155° C./0.2–0.3 mmHg IR (Neat): 2980, 2950, 1740, 1712, 1605 cm$^{-1}$:

$^1$H-NMR (CDCl$_3$) δ: 1.40–1.75 (4H,m), 1.55 (9H, s), 2.15–2.45 (2H,m), 2.50–2.75 (2H,m), 3.62 (3H s), 7.16 (2H,d,J=8 Hz), 7.85 (H,d,J=8 Hz).

Reference Example 2

Production of methyl 5-[4-(tert-butoxycarbonyl)phenyt]-2-iodopentanoate:

Under an atmosphere of argon, to a solution of diisopropylamine (2.48 g) in tetrahydrofuran (100 ml) was added a solution of butyllithium (24.5 mmol) in hexane (15.3 ml) at 0° C. and stirred for 10 minutes; to this a solution of the compound (6.53 g) obtained in the Reference Example 1 in tetrahydrofuran (50 ml) was added dropwise at −78° C. over 30 minutes. After stirring for 30 minutes, a solution of iodine (5.66 g) in tetrahydrofuran (30 ml) was added and stirred for further 20 minutes. The temperature of the solution was brought up to 0° C. over 30 minutes, 1N potassium hydrogen sulfate in water (30 ml) was added dropwise, and the solution was extracted with ether after adjustment to pH 4. The organic layer was washed with 1N potassium carbonate in water and then with saturated sodium chloride solution, and dried with anhydrous magnesium sulfate. The residue obtained by evaporation of the solvent under reduced pressure was purified by column chromatography (ether-hexane, 1:9), to give the object compound (4.736 g).

IR (Neat): 2990, 2905, 1744, 1718, 1612 cm$^{-1}$.

$^1$H-NMR (CDCl$_3$) δ: 1.45–1.80 (2H,m), 1.58 (9H,s), 1.80–2.16 (2H,m), 2.69 (2H,t,J=7 Hz), 3.72 (2H,s), 4.30 (1H,t,J=7 Hz), 7.20 (2H,s,J=8 Hz), 7.90 (2H,d,J=8 Hz).

Reference Example 3

Preparation of methyl 5-[4-(tert-butoxycarbonyl)phenyl]-2-(dicyanomethyl)pentanoate:

To a suspension of sodium hydride (1.356 g) in dimethylsulfoxide (8 ml) was added a solution of malononitrile (3.37 g) in dimethylsulfoxide (8 ml) under cooling with water, and stirred for 15 minutes. To this solution was added dropwise a solution of the compound (4.736 g) obtained in the Reference Example 2 in dimethylsulfoxide (12 ml) and stirred at room temperature for 1 hour, to this 45 ml of 1N potassium hydrogen sulfate in water was added at 0° C., followed by extraction with ether. The ether layer was washed with water and dried with anhydrous magnesium sulfate, followed by evaporation of the solvent under reduced pressure. The residue was purified by column chromatography (carrier; silica gel, 200 g, developing solvent; ethyl acetate: hexane=1:5), to give the object compound (3.33 g).

IR (Neat): 2970, 2930, 2252 1740, 1713, 1608 cm$^{-1}$ $^1$H-NMR (CDCl$_3$) δ: 1.60–2.05 (4H,m), 1.48 (9H,s), 2.70 (2H,brt,J=7 Hz), 2.90–3.15 (1H,m), 3.82 (3H,s), 4.04 (1H, d,J=7 Hz), 7.20 (2H, d,J=8 Hz), 7.92 (2H,d,J=8 Hz).

Reference Example 4

Production of methyl 4-[3-(2-amino-7-benzyl-3isopropyloxymethyl-4(3H)-oxopyrrolo[2,3-d]pyrimidin-5-yl)-1-oxo-2-propenyl]benzoate:

2-Amino-7-benzyl-3-isopropyloxymehtyl-4(3H)-oxopyrrolo[2,3-d]pyrimidine-5-carbaldehyde (1.7 g) was suspended in a methanol-tetrahydrofuran mixture (10:1, 33 ml), to which a solution of sodium methylate in methanol (equivalent to 6.25 mM, 3.75 ml) was added to dissolve. Then 4-methoxycarbonylacetophenone (2.23 g) was added and stirred at room temperature for 15 hours. The precipitate was collected by filtration, washed with a small amount of methanol and ether and dried, to give the object compound (2.02 g) as yellow needles.

IR (KBr): 3480, 3350, 1710, 1680, 1620, 1550 1375, 1280, 1210, 1110, 1060, 775. cm$^{-1}$.

$^1$H-NMR (CDCl$_3$) δ: 1.23 (6H,d,J=6 Hz), 3.93 (3H,s), 3.80–4.07 (1H,m), 5.15 (2H,s), 5.63 (2H,s), 6.92 (1H,s), 7.10–7.40 (5H, m), 7.73 (1H,d,J=15 Hz), 8.13 (4H,s), 8.60 (1H,d,J=15 Hz).

Reference Example 5

Production of methyl 4-[3-(2-amino-3-isopropyloxymethyl-4(3H)-oxo-5,6-dihydropyrrolo-[2,3-d]pyrimidin-5-yl)propyl]benzoate:

The compound (2.01 g) obtained in Reference Example 4 was dissolved in a methanol-tetrahydrofuran mixture (3:4, 350 ml), to which 1N hydrochloric acid (8 ml) and 10% Pd-C (4 g, manufactured by Engelhard Co. Ltd.) were added, and subjected to catalytic reduction under an atmosphere of hydrogen for 48 hours. The catalyst was filtrated off, the filtrate was neutralized, the solvent was evaporated off under reduced pressure and the residue was isolated and purified by column chromatography on silica gel (carrier; 100 g, developing solvent; chloroform containing 2–4% of ethanol), to give the object compound (0.68 g) as a colorless powder.

IR (KBr): 3210, 2980, 1725, 1625, 1580, 1510, 1435, 1275, 1175, 1100, 1060 cm$^{-1}$.

$^1$H-NMR (CDCl$_3$) δ: 1.17(3H,d,J=6 Hz), 1.19 (3H,d,J=6 Hz), 1.50–2.13 (4H,m), 2.70 (2H,t,J=7.5 Hz), 3.07–3.77 (3H,m), 3.80–4.60 (1H,m), 3.87 (3H,s), 5.03 and 5.57 (2H, ABq), 7.21 (2H,d,J=7.5 Hz), 7.91 (2H,d,J=7.5 Hz).

Reference Example 6

Production of menhyl 4-[3-(2-amino-4-hydroxy-5, 6-dihydropyrrolo[2,3-d]pyrimidin-5-yl)propyl]benzoate:

The compound (0.66 g) obtained in the Reference Example 5 was dissolved in dried tetrahydrofuran (31.5 ml), to which 0.21N hydrogen bromide in dichloromethane (78.3 ml) was added and stirred at room temperature for 20 hours. Then 3 volumes of n-hexane was added and the resultant precipitate was collected by filtration, to give the dihydrobomide of the object compound (0.59 g) as a colorless powder.

IR (KBr): 3290, 3030, 2950, 1720, 1690, 1680 1620, 1480, 1350, 1275, 1100, 1035, 760 cm$^{-1}$.

$^1$H-NMR (DMSO-d$_6$) δ: 1.40–1.83 (4H,broad), 2.65 (2H, t,J=7.5 Hz), 3.07–3.37 (2H,m), 3.50–3.77 (1H),m), 3.82 (3H,s), 7.33 (2H,d,J=7.5 Hz), 7.86 (2H,d,J=7.5 Hz).

Reference Example 7

Production of diethyl N-[4-[3-(2-amino-4-hydroxy-5,6-dihydropyrrolo[2,3-d]pyrimidin-5-yl)propyl]benzoyl]-L-glutamate:

The compound (1.47 g) obtained in the Reference Example 6 was suspended in tetrahydrofuran (60 ml), to which 0.1N sodium hydroxide in water (20 ml) was added and stirred at room temperature for 21 hours. Then the solution was neutralized with 0.1N hydrochloric acid (60 ml) and concentrated to dryness under reduced pressure. The residue was suspended in dried dimethylformamide (112.5 ml), to which diethyl L-glutamate hydrochloride (2.88 g), diphenylphosphoryl azide (1.295 ml) and triethylamide (2.52 ml) were added, brought back to the room temperature and stirring was continued for 63 hours. The resulting precipitate was filtrated off, and the filtrate was concentrated to dryness under reduced pressure. The residue was subjected to separation-purification with column chromatography on silica col (carrier; 100 g, developing solvent; chloroform containing 6.9% ammonia-containing ethanol, 1:20–1:10), to give the object compound (1.12 g) as a colorless powder.

IR (KBr): 3330, 2930, 1740, 1670, 1640, 1570, 1540, 1440, 1375, 1300, 1200, 1095, 1020 cm$^{-1}$.

$^1$H-NMR (CDCl$_3$-CD$_3$OD) δ: 1.20 (3H,t,J=7.5 Hz), 1.27 (3H,t,J=7.5 Hz), 1.47–1.83 (4H,m), 2.0–2.36 (2H,m), 2.37–2.50 (2H,m), 2.67 (2H,t,J=7.5 Hz), 3.10–3.37 (2H,m), 3.53–3.80 (1H,m), 3.96–4.33 (4H,q×2,J=7.5 Hz), 4.60–4.87 (1H,m), 7.25 (2H,d, J=9 Hz), 7.75 (2H,d,J=9 Hz).

Reference Example 8

Production of methyl 4-[3-(2-amino-7-benzyl-3-isopropyloxymethyl-4(3H)-oxopyrrolo[2,3-d]pyrimidin-5-yl)-1-oxo-2-propenyl]benzoate:

2-Amino-7-benzyl-3-isopropyloxymethyl-4(3H)-oxopyrrolo[2,3-d]pyrimidine-5-carbaldehyde (1.7 g) was suspended in a methanol-tetrahydrofuran mixture (10:1, 33 ml), to which a solution of sodium methylate in methanol (equivalent to 6.25 mM, 3.75 ml) was added to dissolve. Then 4-methoxycarbonylacetophenone (2.23 g) was added and stirred at room temperature for 15 hours. The precipitate was collected by filtration, washed with s small amount of methanol and ether, and dried, to give the object compound (2.02 as yellow needles.

IR (KBr): 3480, 3350, 1710, 1680, 1620, 1550, 1375, 1280, 1210, 1110, 1060, 775 cm$^{-1}$ $^1$H-NMR (CDCl$_3$) δ: 1.23 (6H,d,J=6 Hz), 3.93 (3H,s), 3.80–4.07 (1H,m), 5.15 (2H,s), 5.63 (2H,s), 6.92 (1H,s), 7.10–7.40 (5H,m), 7.73 (1H,d,J=15 Hz), 8.13 (4H,s), 8.60 (1H,d,J=15 Hz).

Reference Example 9

Production of methyl 4-[3-(2-amino-3-isopropyloxymethyl-4(3H)-oxo-5,6-dihydropyrrolo[2,3-d]pyrimidin-5-yl) propyl]benzoate:

The compound (2.01 g) obtained in Reference Example 8 was dissolved in a methanol-tetrahydrofuran mixture (3:4, 350 ml), to which 1N hydrochloric acid (8 ml) and 10% Pd-C (4 g, manufactured by Engelhard Co. Ltd.) were added, and subjected to catalytic reduction under an atmosphere of hydrogen for 48 hgurs. The catalyst was filtrated off, the filtrate was neutralized, the solvent was evaporated off under reduced pressure, and the residue was isolated and purified by column chromatography on silica gel (carrier; 100 g) (developing solvent: chloroform containing 2–4% of ethanol), to give the object compound (0.68 g) as a colorless powder.

IR (KBr): 3210, 2980, 1725, 1625, 1580, 1510, 1435, 1275, 1175, 1100, 1060 cm$^{-1}$.

$^1$H-NMR (CDCl$_3$) δ: 1.17 (3H,d,J=6 Hz), 1.19(3H,d,J= 6Hz), 1.50–2.13 (4H,m), 2.70 (2H,t,J=7.5 Hz), 3.07–3.77 (3H,m), 3.80–4.06 (1H,m), 3.87 (3H,s), 5.03 and 5.57 (2H, ABq), 7.21 (2H,d,J=7.5 Hz), 7.91 (2H,d,J=7.5 Hz).

Reference Example 10

Production of methyl 4-[3-(2-amino-4-hydroxy-5,6-dihydropyrrolo[2,3-d]pyrimidin-5-yl)propyl]benzoate:

The compound (0.66 g) obtained in the Reference Example 9 was dissolved in dried tetrahydrofuran (31.5 ml), to which 0.21N hydrogen bromide acid in dichloromethane (78.3 ml) was added, and stirred at room temperature for 20 hours. Then 3 volumes of n-hexane was added and the resultant precipitate was collected by filtration, to give the dihydrobromide of the object compound (0.59 g) as a colorless powder.

IR (KBr): 3290, 3030, 2950, 1720, 1690, 1680, 1620, 1480, 1350, 1275, 1100, 1035, 760 cm$^{-1}$.

$^1$H-NMR (DMSO-d$_6$) δ: 1.40–1.83 (4H, broad), 2.65 (2H,t,J=7.5 Hz), 3.07–3.37 (2H,m), 3.50–3.77 (1H,m), 3.82 (3H,s), 7.33 (2H,d,J=7.5 Hz), 7.86 (2H,d,J=7.5 Hz).

Reference Example 11

Production of methyl 4-[2-(2-amino-7-benzyl-3-isopropyloxymethyl-4(3H)-oxopyrrolo[2,3-d]pyrimidin-5-yl)ethenyl]benzoate:

To the suspension of 2-amino-7-benzyl-3-isopropyloxymethyl-4(3H)-oxopyrrolo[2,3-d]pyrimidine-5-carbaldehyde (2.04 g) in dried methanol (84 ml) was added p-methoxycarbonylbenzyltriphenylphosphonium bromide (3.24 g) and stirred. Then a solution of sodium methylate in methanol (equivalent to 6.6 mM on sodium basis) was added and stirred at room temperature for 1.5 hours, to give yellow needles. The needles were collected by filtration, washed with methanol and then with ether, and dried, to give the object product (cis-form, 1.49 g). The mother liquor was purified by column chromatography on silica gel (carrier: 100 g) (developing solvent: ethyl acetate-hexane, 1:4–1:3), to give the cis-trans mixture of the object compound (0.9 g) as yellow powders. cis-form;

IR (KBr): 33.40, 3220, 2980, 1715, 1690, 1625, 1600, 1530, 1430, 1280, 1175, 1105, 1060, 995 cm$^{-1}$.

$^1$H-NMR (CDCl$_3$) δ: 1.20 (6H,d,J=6 Hz), 3.87 (3H,s), 3.80–4.07 (1H,m), 5.14 (2H,s), 5.32 (2H,s), 5.60 (2H,s), 6.77 (1H,s), 7.10–7.37 (5H,m), 7.43 (2H,s), 7.50 (2H,d,J=9 Hz), 7.95 (2H,d,J=9 Hz).

Reference Example 12

Production of methyl 4-[2-(2-amino-3-isopropyloxy methyl-4(3H)-oxo-5,6-dihydropyrrolo[2,3-d]pyrimidin-5-yl)ethyl]benzoate:

The compound (1.6 g) obtained in the Reference Example 11 was subjected to the same reaction to that in the Reference Example 9, to give the object compound (0.62 g).

$^1$H-NMR (CDCl$_3$) δ: 1.17 (3H,d,J=6 Hz), 1.20 (3H,d,J=6 Hz), 1.47–2.0 (1H,m), 2.10–2.43 (1H,m), 2.65 (2H,t,J=9 Hz), 2.97–3.60 (3H,m), 3.73–4.07 (1H,m), 3.90 (3H,s), 4.47 (2H,s), 5.30 (1H,d,J=12 Hz), 5.60 (1H,d,J=12 Hz), 7.13–7.50 (7H,m), 7.92 (1H,d,J=9 Hz)

Reference Example 13

Production of methyl 4-[2-(2-amino-4-hydroxy-7H-5,6-dihydropyrrolo[2,3-d]pyrimidin-5-y1)ethyl]benzoate:

The compound (1.25 g) obtained in the Reference Example 12 was subjected to the same reaction to that in the Reference Example 10, to give the object compound (0.5g).

IR (KBr): 3400, 3300, 2920, 1740, 1710, 1680, 1640, 1600, 1570, 1435, 1310, 1280, 1110, 1020 cm$^{-1}$.

$^1$H-NMR (DMSO-d$_6$/D$_2$O) δ: 1.53–2.27 (2H,m), 2.70 (2H,t,J=9 Hz), 3.00–3.26 (2H,m) 3.47–3.63 (1H,m), 3.83 (3H,s), 7.35 (2H,d J=9 Hz), 7.85 (2H,d,J=9 Hz),

Reference Example 14

Production of methyl 5-[4-(tert-butoxycarbonyl)phenyl] pentanoate:

Under an atmosphere of argon, potassium (25 g) was dissolved completely in dried tert-butyl alcohol (820 ml) by refluxing by heating for 3 hours. The solution was cooled to 20° C., to which was added ether (300 ml) and then slowly a solution of methyl crotonate (63.93 g) and cert-butyl 4-formylbenzoate (71.0 g) in tert-butyt alcohol-ether mixture (2:1, 300 ml) while keeping the inner temperature at 10° C.

The mixture was stirred at the same temperature for 2 hours, and 1N potassium hydrogen sulfate in water (750 ml) was added with cooling to adjust the pH to 4. After extraction with ether, the ether layer was washed with saturated sodium chloride solution and the solvent was evaporated off under reduced pressure. The residue was dissolved in ethyl acetate (100 ml), to which was added 5% Pd-C (15 g: manufactured by Engelhard Co. Ltd.), and stirred vigorously at room temperature under hydrogen pressure of 4 kg/cm$^2$ for 3 hours. The catalyst was filtered off, the solvent was evaporated off under reduced pressure, and dried methanol (200 ml), 4-(N,N-dimethylamino)pyridine (30 mg) and dichloromethane (250 ml) were added, to which a solution of 1,3-dicyclohexylcarbodiimide (132 q) in dichloromethane (250 ml) was added slowly dropwise at 0° C. After stirring at room temperature for 18 hours, the mixture was cooled to 0° C. Acetic acid (30 ml) was added and the mixture stirred at 0° C. for 30 minutes and then at room temperature for 30 minutes. The resulting precipitate was filtered off, the filtrate was concentrated to dryness under reduced pressure, and to the residue was added ethyl acetate (100 ml, which was left standing at 0° C. for 2 hours, and the resulting precipitate was again filtered off. The Filtrate was concentrated under reduced pressure, and the residue was purified by column chromatography (carrier: silica gel, 500 g, ether-hexane, 1:15–1:5), to give the object compound (59.7 g).

Bp. 145°–155° C./0.2–0.3 mmHg.

IR (Neat): 2980, 2950, 1740, 1712, 1605 cm$^{-1}$.

$^1$H-NMR (CDCl$_3$) δ: 1.40–1.75 (4H,m), 1.55 (9H,s), 2.15–2.45 (2H,m), 2.50–2.75 (2H,m), 3.62 (3H,s), 7.16 (2H,d,J=8 Hz), 7.85 (H,d,J=8 Hz).

Reference Example 15

Production of methyl 5-[4-(tert-butoxycarbnyl)phenyl]-2-iodopentanoate:

Under an atmosphere of argon, a solution of butyllithium (24.5 mmol) in hexane (15.3 ml) was added to a solution of diisopropylamine (2.48 g) in tetrahydrofuran (100 ml) at 0° C. and stirred for 10 minutes. To the resultant solution was added a solution of the compound (6.53 g) obtained in the Reference Example 14 in tetrahydrofuran (50 ml) at −78° C. dropwise over 30 minutes. After stirring for 30 minutes a solution of iodine (5.66 g) in tetrahydrofuran (30 ml) was added and stirred for further 20 minutes. The temoerature was increased to 0° C. over 30 minutes, 30 ml of 1N potassium hydrogen sulfate in water was added dropwise, and the pH was adjusted to 4, followed by extraction with ether. The organic layer was washed with 1N potassium carbonate in water and then with saturated sodium chloride solution, and dried with anhydrous magnesium sulfate. The solvent was evaporated off under reduced pressure, and the resultant residue was purified by column chromatography (carrier: silica gel, 100 g, ether-hexane, 1:9), to give the object compound (4.736 g).

IR (Neat): 2990, 2905, 1744, 1718, 1612 cm$^{-1}$.

$^1$H-NMR (CDCl$_3$) δ: 1.45–1.80 (2H,m), 1.58 (9H,s), 1.80–2.16 (2H m), 2.69 (2H,t,J=7 Hz), 3.72 (2H,s), 4.30 (1H,t,J=7 Hz), 7.20(2H,d,J=8 Hz), 7.90(2H d J=8 Hz)

Reference Example 16

Production of methyl 5-[4-(tert-butoxycarbonyl)-phenyl] -2-(dicyanomethyl)pentanoate:

To a suspension of sodium hydride (1.356 g) in dimethylsulfoxide (8 ml) was added a solution of malononitrile (3.37 g) in dimethytsulfoxide (8 ml) with ice-cooling and stirred for 15 minutes. To the solution was added a solution of the compound (4.736 g) obtained in the Reference Example 15 in dimethylsulfoxide (12 ml) dropwise, and the mixture was stirred at room temperature for 1 hour. Then 45 ml of 1N potassium hydrogen sulfate in water was added at 0° C., followed by extraction with ether. The ether layer was washed with water and dried with anhydrous magnesium sulfate. The residue obtained by evaooration of the solvent under reduced oressure was purified by column chromatography (carrier: silica gel, 200 g, ethyl acetate-hexane, 1:5), to give the object compound (3.33 g).

IR (Neat): 29.70, 2930, 2252, 1740, 1713, 1608 cm$^{-1}$.

¹H-NMR (CDCl₃) δ: 1.60–2.05 (4H,m), 1.48 (9H,s), 2.70 (2H,brt,J=7 Hz), 2.90–3.15 (1H,m), 3.82(3H,s), 4.04(1H,d, J=7 Hz), 7.20(2H,d,J=8 Hz), 7.92(2H,d,J=8 Hz).

Reference Example 17

Production of ethyl 5-[4-(tert-butoxycarbonyl)-phenyl] hexanoate:

In a solution of tert-butyl 4-acetylbenzoate (19.90 g) in a benzene-ether-tetrahydrofuran mixture (3:3:2, 200 ml) was suspended zinc (11.81 g), to which ethyl 4-bromocrotonate (17.44 g) was added slowly while heating and stirring, and then iodine (about 20 mg) was added. The resulting mixture was refluxed by heating on an oil bath (60°–70° C.) for 1 hour, then ethyl 4-bromocrotonate (3.00 g) was added, and the mixture was further refluxed by heating for 15 minutes. After cooling to room temperature, the reaction mixture was added to water (500 ml), adjusted to pH 4.9 by addition of acetic acid and extracted with ether. The extract was washed with 5% aqueous ammonia and dried with anhydrous magnesium sulfate.

The residue obtained by evaporation of the solvent under reduced pressure was purified by column chromatography (carrier; silica gel, 300 g, developing solvent; ethyl acetate-hexane=1:5), to give the object compound.

IR (Neat): 3480, 2975, 1720, 1700, 1550, 1505 cm⁻¹.

¹H-NMR (CDCl₃) δ: 1.20 (3H,t,J=7 Hz), 1.53 (12H,s), 2.64 (2H,d,J=7 Hz), 2.67 (1H,brs), 3.63 (3H,s), 4.08 (2H,q, J=7 Hz), 5.80 (1H,d,J=15 Hz), 6.80 (1H,dt,J=15 Hz 7 Hz), 7.45 (2H,d,J=8 Hz), 7.90 (2H,d,J=8 Hz).

The entire amount of ethyl hexenate derivative (22.3 g) was dissolved in an ethanol-acetic acid mixture (20:1, 200 ml), to which 5% Pd-C (5.0 g) was added, then was stirred vigorously for 115 hours. After filtration of Pd-C using celite and evaporation of solvent under reduced pressure, the residue was subjected to evaporation under reduced pressure, to give the object compound (15.66 g) as a colorless oil. Bp. 162°–165° C./0.3 mmHg IR (Neat): 2980, 2940, 1735, 1710, 1607, 848 cm⁻¹.

¹H-NMR (CDCl₃) δ: 1.20 (3H,t,J=7 Hz), 1.23 (3H,d, J=6 Hz), 1.30–1.80 (4H,m), 1.58 (9H,s), 2.24 (2H,brt,J=6 Hz), 2.77 (1H,dq,J=6 Hz, 6 Hz), 4.08 (2H,q,J=7 Hz), 7.20 (2H, d,J=8 Hz), 7.90 (2H,d,J=8 Hz).

Reference Example 18

Production of ethyl 5-[4-(tert-butoxycarbonyl)phenyl]-2-iodohexanate:

The compound (6.41 g) obtained in the Reference Example 17 was subjected to the same reaction as that in the Reference Example 2 to give the object compound (3.90 g).

IR (Neat): 2980, 2940, 1738, 1715, 1610, 850 cm⁻¹.

¹H-NMR (CDCl₃) δ: 1.23 (3H t J=7 Hz), 1.23 (2H,d,J=7 Hz), 1.40–1.95 (4H,m), 1.60 (9H,s), 2.75 (1H,dq,J=6 Hz,6 Hz), 4.15 (2H,q,J=7 Hz), 4.18 (1H,t,J=7 Hz), 7.20 (2H,d,J=8 Hz), 7.90 (2H,d,J=8 Hz).

Reference Example 19

Production of ethyl 5-[4-(tert-butoxycarbonyl)phenyl]-2-(dicianomethyl)-hexanoate:

The compound (3.90 g) obtained in the Reference Example 18 was subjected to the same reaction as that in the Reference Example 3 to give the object compound (3.19 g).

IR (Neat): 2980, 2930, 2250, 1735, 1710, 1605, 847 cm⁻¹.

¹H-NMR (CDCl₃) δ: 1.26 (1 5H,t,J=7 Hz), 1.26 (3H,d,J=7 Hz), 1.27 (1.5H,t,J=7 Hz), 1.35–1.80 (4H,m), 1.58 (9H,s), 2.50–3.08 (2H,m), 4.00 (1H,dd,J=8 Hz,4 Hz), 4.22 (1H,q, J=7 Hz), 4.23 (1H,q,J=7 Hz), 7.18 (2H,d,J=8 Hz), 7.92 (2H,d,J=8 Hz).

Working Example 1

Production of tert-butyl 4-[3-(2,4-diamino-6-hydroxy-7H-pyrrolo[2,3-d]pyrimidin-5-yl)propyl]benzoate:

To a solution of potassium tert-butoxide (2.35 g) and guanidine hydrochloride (1.07 g) in tert-butylalcohol (10 ml) was added a solution of the compound (3.33 g) obtained in the Reference Example 3 in tert-butyl alcohol (30 ml) under an atmosphere of argonr and refluxed by heating for 20 hours. To the reaction mixture were added further potassium tert-butoxide (434 mg) and guanidine hydrochloride (370 mg) and the mixture was refluxed by heating for 8 further hours. The reaction mixture was cooled, added to 1N potassium hydrogen sulfate in water (about 10 ml) and adjusted to pH 9. After extraction with a tetrahydrofuran-chloroform mixture, the solvent was evaporated off under reduced pressure and the resultant residue was purified by column chromatography (carrier; silica gel, 100 g, developing solvent; dichloromethane: ethanol=15:1→dichloromethane after mixing with concentrated aqueous ammonia in a separatory funnel: ethanol=15:1), to give the object compound (1.90 g).

IR (KBr): 3430, 3360, 1710, 1627, 1583, 1432 cm⁻¹.

¹H-NMR (CDCl₃-Me₂SO-d₆) δ: 1.15–1.73 (2H,m), 1.55 (9H,s), 1.73–2.10 (2H,m), 2.61 (2H,t,J=7 Hz), 3.35 (1H,t, J=6 Hz), 5.40 (2H,brs), 5.51 (2H,brs), 6.30 (1H,brs), 7.12 (2H,d,J=8 Hz), 7.29 (2H,d,J=8 Hz).

Working Example 2

Production of tert-butyl 4-[3-(2,4-diamino-7H-pyrrolo[2,3-d]pyrimidin-5-yl)propyl]benzoate:

To a solution of the compound (575 mg) obtained in the Working Example 1 in tetrahydrofuran (6 ml) was added a solution of borane-tetrahydrofuran complex (7.5 mmol) in tetrahydrofuran (7.5 ml) at 0° C., and stirred for 4.5 hours. To the reaction mixture was added acetic acid-methanol (1:1, 6 ml) and the mixture was stirred at room temperature for 15 hours. The solvent was evaporated off under reduced pressure and the residue was purified by column chromatography (carrier; silica gel, 30 g, developing solvent; dichloromethane: ethanol=100:6 →100:7→100:8→10:1→ 8:1), to give the object compound (263 mg).

IR (KBr): 3335, 3180, 2975, 2935, 1710, 1607, 1287, 1163, 1110 cm⁻¹.

¹H-NMR (Me₂SO-d₆) δ: 1.54 (9H,s), 1.77–1.90 (2H,m), 2.68(2H,t,J=8 Hz), 2.72 (2H,t,J=8 Hz), 5.54 (2H,brs), 6.11 (2H,brs), 6.45 (1H,s), 7.33 (2H,d,J=8 Hz), 7.82 (2H,d,J=8 Hz), 10.51 (1H,s).

Working Example 3

Production of diethyl N-[4-[3-(2,4-diamino-7H-pyrrolo [2,3-d]pyrimidin-5-yl)propyl]benzoyl]-L-glutamate:

To the compound (381 mg) obtained in the Working Example 2 was added trifluoroacetic acid (3 ml) and the mixture was stirred at room temperature for 3 hours. Trifluoroacetic acid was evaporated off under reduced pressure, and to the residue obtained by drying at 70° C. under reduced pressure and a solution of diethyl L-glutamate hydrochloride (748 mg) in dimethylformamide (4 ml) was added a solution of diphenylphosphoryl azide (858 mg) in dimethylformamide (4 ml) at 0° C., and then a solution of triethylamine (631 mg) in dimethylformamide (4 ml) dropwise at the same temperature. After stirring at 0° C. for 30 minutes and then at room temperature for 63 hours, the precipitate was filtered off. The solvent was evaporated off under reduced pressure and the resultant residue was purified by column chromatography (carrier; silica gel, 20 g, developing solvent; dichloromethane after mixing with concentrated aqueous ammonia in a separatory funnel→dichloromethane after mixing with concentrated aqueous ammonia: ethanol=40:1→30:1), to give the object compound (260 mg).

IR (KBr): 3330, 3160, 1735, 1632, 1575, 1540, 1500, 1200 cm$^{-1}$.

$^1$H-NMR (Me$_2$SO-d$_6$) δ: 1.17(3H,t,J=7 Hz), 1.20 (3H,t, J=7 Hz), 1.80–2.20 (4H,m), 2.44 (2H,t,J=7 Hz), 2.68 (2H,t, J=7 Hz), 2.72 (2H,t,J=7 Hz), 4.05 (2H,q,J=7 Hz), 4.11 (2H,q,J=7 Hz), 4.35–4.80 (1H,m), 5.34 (2H,s), 5.91 (2H,s), 6.42 (1H,s), 7.31 (2H,d,J=8 Hz), 7.80 (2H,d,J=8 Hz), 8.86 (1H,d,J=8 Hz), 10.51 (1H,s).

Working Example 4

Production of N-[4-[3-(2,4-diamino-7H-pyrrolo [2,3-d] pyrimidin-5-yl)propyl]benzoyl]-L-glutamic acid:

The compound (250 mg) obtained in the Working Example 3 was dissolved in tetrahvdrofuran-water mixture (1:1, 7 ml), to which 1N sodium hydroxide in water (2.52 ml) was added and the mixture was stirred at room temperature for 1.5 hours. The solution was concentrated to 3 ml under reduced pressure, and the resultant insoluble matter was filtrated off through a millipore filter. To the filtrate, cooled to 0° C., was added acetic acid (0.5 ml) and the resultant crystals were collected by filtration and washed throughly with ice-water. The crystals were dried at 70° C. under reduced pressure, to give the object compound (201 mg) as white crystals.

IR (KBr): 3340, 3200, 2940, 1660–1630, 1540, 1500, 1397 cm$^{-1}$.

$^1$H-NMR (Me$_2$:SO-d$_6$) δ: 1.75–2.20 (4H,m), 2.35 (2H,t, J=7 Hz), 2.68 (2H,t,J=7 Hz), 2.71 (2H,t,J=7 Hz), 4.30–4.47 (1H,m), 5.53 (2H,brs), 6.15 (2H,s), 6.46 (1H,s), 7.31 (2H, d,J=8 Hz), 7.81 (2H,d,J=8 Hz), 8.48 (1H,d,J=8 Hz); 10.51 (1H,s).

Working Example 5

Production of diethyl N-[4-[3-(2,4-diamino6-hydroxy-7H-pyrrolo[2,3-d]pyrimidin-5-yl) propyl]benzoyl]-L-glutamate:

The compound (200 mg) obtained in the Working Example 1 was subjected to the same reaction as that in the Working Example 3, to give the object compound (164 mg).

IR (KBr): 3355, 3230, 2995, 2990, 1740, 1638, 1595, 1590 cm$^{-1}$.

$^1$H-NMR (CDCl$_3$/Me$_2$SO-d$_6$) δ: 1.20 (3H,t,J=7 Hz), 1.25 (3H,t, J=7 Hz), 1.25–2.70 (11H,m), 3.25–3.45 (1H,m), 4.0 5 (2H,q,J=7 Hz), 4.15 (2H,q,J=7 Hz), 4.38–4.68 (1H,m), 5.63 (2H,brs), 5.66 (2H, brs), 7.16 (2H,d, J=8 Hz), 7.76 (2H, d, J=8 Hz), 8.39 (1H,d, J=8 Hz), 10.50 (1H,s).

Working Example 6

Production of N-[4-[3-(2,4-diamino-6-hydroxy- 7H-pyrrolo[2,3-d]pyrimidin-5-yl)propyl]benzoyl]-L-glumatic acid:

The compound (112 mg) obtained in the Working Example 5 was subjected to the same reaction as that in the Working Example 4, to give the object compound (60 mg).

IR (KBr): 3350, 3210, 2950, 1730, 1660, 1630 cm$^{-1}$.

$^1$H-NMR (Me$_2$SO-d$_6$) δ: 1.20–1.56 (2H,m), 1.65–2.20(4H,m), 2.35 (2H,t,J=7 Hz), 2.50–2.65 (2H,m), 3.25–3.35 (1H,m), 4.32–4.46 (1H,m), 5.90 (2H,brs), 6.00 (2H,brs). 7.22 (2H,d,J=8 Hz), 7.78 (2H,d,J=8 Hz), 8.52 (1H,d,J=8 Hz), (1H,s).

Working Example 7

Production of diethyt N-[4-[3-(2-amino-4-hydroxy-7H-pyrrolo[2,3-d]pyrimidin-5-yl)propyl]benzoyl]-L-glutamate:

The compound (150 mg) obtained in the Reference Example 7 was dissolved in ethanol (22.5 ml), to which were added 10% Pd-C (450 mg: manufactured by Engelhand Co. Ltd.) and 2 drops of acetic acid and stirred vigorously at room temperature for 62.5 hours. The catalyst was filtered off, the filtrate was concentrated to dryness and the residue was purified by column chromatography (carrier; silica gel, 10 g, developing solvent; chloroform containing 5% ethanol), to give the object compound (33 mg).

IR (KBr): 3340, 2940, 1740, 1680, 1630, 1540, 1440, 1380, 1340, 1210, 1100, 1020, 860 cm$^{-1}$.

$^1$H-NMR (CDCl$_3$/CD$_3$OD) δ: 1.20 (3H,t,J=6 Hz), 1.28 (3H,t,J=6 Hz), 1.87–2.36 (4H,m), 2.40–2.57 (2H,m), 2.60–2.87 (4H,m), 3.96–4.37 (4H,q x 2,J=6 Hz), 4.56–4.90 (1H,m), 6.37 (1H,s), 7.23 (2H,d,J=7.5 Hz), 7.71 (2H,d,J=7.5 Hz).

Working Example 8

Production of N-[4-[3-(2-amino-4-hydroxy-7H-pyrrolo [2,3-d]pyrimidin-5-yl)propyl]benzoyl]-L-glutamic acid:

The compound (27 mg) obtained in the Working Example 7 was dissolved in a tetrahydrofuran-water mixture (1:1, 2.16 ml), to which was added 1N sodium hydroxide in water (0.189 ml) and stirred at room temperature for 2.5 hours. A large portion of tetrahydrofuran was evaporated off, acetic acid (0.189 ml) was added by ice-cooling and stirred. The resulting precipitate was collected by filtration and dried, to give the object compound 19 mg)

IR (KBr): 3400, 3300, 2950, 1700, 1650, 1540, 1510, 1400, 1340, 1240, 1080, 1020 cm$^{-1}$ $^1$H-NMR (Me$_2$SO-d$_6$) δ: 1.80–2.17 (4H,m), 2.23–2.40 (2H,m), 2.53–2.83 (4H,m), 4.27–4.56 (1H,m), 6.33 (1H,s), 7.27 (2H,d,J=7.5 Hz), 7.78 (2H,d,J=7.5 Hz).

Working Example 9

Production of tert-butyl 4-[3-(2,4-diamino-6-oxo-5,6-dihydropyrrolo[2,3-d]pyrimidin-5-yl)propyl]benzoate:

To a solution of potassium tert-butoxide (2.35 g) and guanidine hyrochloride (1.07 g) in tert-butyl alcohol (10 ml) was added a solution of the compound (3.33 g) obtained in the Reference Example 16 in tert-butyl alcchol (30 ml) under an atmosphere of argon, and refluxed by heating for 20 hours. To the reaction mixture were added further potassium tert-butoxide (434 mg) and guanidine hydrochloride (370 mg), and refluxed by heating for further 8 hours. The reaction mixture was cooled, added to 1N potassium hydrogen sulfate in water (about 10 ml), to be adjusted to pH 9. After extraction with a tetrahydrofuran-chloroform mixture, the solvent was evaporated off under reduced pressure, and the resultant residue was purified by column chromatography (carrier; silica gel, 100 g, dichloromethane-ethanol, 15:1 dichloromethane after mixing with concentrated aqeous ammonia in a separatory funnel-ethanol, 15:1), to give the object compound (1.90 g).

IR (KBr): 3430, 3360, 1710, 1527, 1583, 1432 cm$^{-1}$.

$^1$H-NMR (CDCl$_3$/Me$_2$SO-d$_6$) δ: 1.15–1.73 (2H,m), 1.55 (9H,s), 1.73–2.10 (2H,m), 2.61 (2H,t,J=7 Hz), 3.35 (1H,t, J=6 Hz), 5.40 (2H,brs), 5.51 (2H,brs), 6.30 (1H,brs), 7.12 (2H,d,J=8 Hz), 7.29(2H,d,J=8 Hz).

Working Example 10

Production of tert-butyl 4-[3-(2,4-diamino-5,6-dihydro-pyrroio[2,3-d]pyrimidin-5-yl)propyl]benzoate:

To a solution of the compound (430 mg) obtained in the Working Example 9 in tetrahydrofuran (10 ml) was added a solution of borane-tetrahydrofuran complex (16.8 mmol) in tetrahydrofuran (10 ml) and the mixture was refluxed by heating for 4 hours. After cooling, the reaction mixture was added to ice water and stirred vigorously at pH 2 (adjusted by addition of 1N hydrochloric acid) for 3 minutes and then at pH 10.5 (adjusted by addition of 2N potassium carbonate in water) for 5 minutes. The reaction mixture was extracted with tetrahydrofuran-chloroform mixture. The solvent was evaporated off under reduced pressure, and the residue was purified by column chromatography (carrier; silica gel, 20 g, dichloromethane-ethanl, 30:1→15:1 dichloromethane after mixing with concentrated aqueous ammonia in a separatory funnel-ethanol, 20:1), to give the object compound (114 mg).

IR (KBr): 3375, 3325, 3190, 2970, 2930, 1712, 1603 cm$^{-1}$.

$^1$H-NMR (CDCl$_3$/Me$_2$SO-d$_6$) δ: 1.45–2.15 (4H,m), 1.57 (9H,s), 2.65 (2H,t,J=7 Hz), 3.00–3.28 (2H,m), 3.44–3.70 (1H,m), 4.85 (2H,brs), 4.90 (2H,brs), 5.30 (1H,brs), 7.19 (2H,d,J=8 Hz), 7.80 (2H,d,J=8 Hz).

Working Example 11

Production of diethyl N-[4-[3-(2-amino-4-hydroxy-5,6-dihydropyrrolo[2,3-d]pyrimidin-5-yl)propyl]benzoyl]-L-glutamate:

The compound (1.47 g) obtained in the Reference Example 10 was suspended in tetrahydrofuran (60 ml), to which 0.1N sodium hydroxide in water (120 mt) was added, and the mixture was stirred at room temperature for 2 hours. Then the solution was neutralized with 0.1N hydrochloric acid (60 ml) and concentrated to dryness under reduced pressure. The residue was suspended in dried dimethylformamide (112.5 ml), to which diethyl L-glutamate hydrochloride (2.88 g), diphenylphosphoryl azide (1.295 ml) and triethylamine (2.52 ml) were added. The mixture was brought back to the room temperature, and stirring was continued for 63 hours. The resulting precipitate was filtered off, and the filtrate was concentrated to dryness under reduced pressure. The residue was subjected to separation-purification with column chromatography on silica gel (carrier; 100 g) (ethanol containing 6.9% ammonia-chloroform containing 6.9% ammonia, 1:20→1:10), to give the object compound (1.12 g) as a colorless powder.

IR (KBr): 3330, 2930, 1740, 1670, 1640, 1570, 1540, 1440, 1375, 1300, 1200, 1095, 1020 cm$^{-1}$.

$^1$H-NMR (CDCl$_3$/CD$_3$OD) δ: 1.20 (3H,t,J=7.5 Hz), 1.27 (3H,t,J=7.5 Hz), 1.47–1.83 (4H,m), 2.00–2.36 (2H,m), 2.37–2.50 (2H,m), 2.67 (2H t J=7.5 Hz), 3.10–3.37 (2H m), 3.53–3.80 (1H,m), 3.96–4.33 (4H,qx2,J=7.5 Hz), 4.60–4.87 (1H,m), 7.25 (2H,d,J=9 Hz), 7.75 (2H,d,J=9 Hz).

Working Example 12

Production of diethyl N-[4-[2-(2-amino-4-hydroxy-5,6-dihydropyrrolo[2,3-d]pyrimidin-5-yl)ethyl]benzoyl]L-glutamate:

The compound (0.315 g) obtained in the Reference Example 13 was subjected to the same reaction as that in the Working Example 11, to give the object compound (0.247 g).

IR (KBr): 3310, 2990, 1740, 1730, 1690, 1640, 1570, 1530, 1440, 1375, 1330, 1300, 1240, 1200, 1090, 1010, 850 cm$^{-1}$.

$^1$H-NMR (CDCl$_3$/CD$_3$OD) δ: 1.22 (3H,t,J=7.5 Hz), 1.30 (3H,t,J=7.5 Hz), 1.53–2.87 (8H,m), 3.13–3.90 (3H,m), 4.00–4.43 (4H,qx2,J=7.5 Hz), 4.57–4.90 (1H,m), 7.25 (2H, d,J=9 Hz), 7.72 (2H,d,J=9 Hz).

Working Example 13

Production of diethyl N-[4-[3-(2,4-diamino-5,6-dihydro-pyrrolo[2,3-d]pyrimidin-5-yl)propyl]benzoyl]L-glutamate:

The compound (94 mg) obtained in the Working Example 10 was dissolved in 1 ml of trifluoroacetic acid and stirred at room temperature for 3 hours. The solvent was evaporated off under reduced pressure, and to the mixture of the residue obtained by drying at 70° C. under reduced pressure and diethyl L-glutamate (304 mg) in dimethylformamide (2 ml), was added a solution of diphenylphosphoryl azide (350 mg) in dimethylformamide (1.5 ml) at 0° C., and then a solution of triethylamine (180 mg) in dimethylformamide (1.5 ml) dropwise at the same temperature. After stirring at 0° C. for 30 minutes and then at room temperature for 78 hours, the solvent was evaporated off under reduced pressure. The resultant residue was purified by column chromatography (carrier; silica gel, 20 g, dichloromethane after mixing with concentrated aqueous ammonia in a separatory funnel→ dichloromethane after mixing with concentrated aqueous ammonia —ethanol 40:1→30:1), to give the object compound (88 mg).

IR (KBr): 3350, 2990, 2945, 1740, 1610, 1540, 1508, 1438 cm$^{-1}$.

$^1$H-NMR (CDCl$_3$) δ: 1.23 (H,g,J=7 Hz), 1.43–1.80 (3H, m), 1.85–2.77 (7H,m), 2.95–3.30 (2H,m), 3.58 (1H,t,J=11 Hz), 4.07 (2H,q,J=7 Hz), 4.20 (2H,q,J=7 Hz), 4.25 (1H,brs), 4.63–4.83 (1H,m), 4.68 (1H,brs), 7.00–7.23 (1H,m), 7.13 (2H,d,J=8 Hz), 7.67 (2H,d,J=8 Hz).

Working Example 14

Production of N-[4-[3-(2-amino-4-hydroxy-5,6-dihydro-pyrrolo[2,3-d]pyrimidin-5-yl)propyl]henzoyl]L-glutamic acid:

The compound (1.05 g) obtained in the Working Example 11 was dissolved in tetrahydrofuran-water mixture (2:1, 63 ml), to which 1N sodium hydroxide in water (7.35 ml) was added, and stirred at room temperature for 2.5 hours. Tetrahydrofuran was evaporated off, a small amount of insoluble matter was filtrated off, acetic acid (7.35 ml) was added to the filtrate, and the resulting precipitate was collected by filtration. The precipitate was washed. with water and dried, to give the object compound (0.85 g) as a colorless powder.

IR (KBr): 3340, 2930, 1690, 1630, 1540, 1440, 1300, 1080, 850 cm$^{-1}$.

$^1$H-NMR (DMSO-d$_6$) δ: 1.20–1.80 (4H,m), 1.87–2.17 (2H,m), 2.23–2.40 (2H,m), 2.50–2.77 (2H,m), 2.83–3.20 (2H,m), 3.30–3.63 (1H,m), 4.23–4.53 (1H,m), 7.26 (2H,d, J=9 Hz), 7.77 (2H,d,J=9 Hz).

Working Example 15

Production of N-[4-[2-(2-amino-4-hydroxy-5,6-dihydropyrrolo[2,3-d]pyrimidin-5-yl)ethyl]benzoyl]-L-glutamic acid:

The compound (0.195 g) obtained in the Working Example 12 was subjected to the same reaction as that in the Working Example 14, to give the object compound (0.153 g).

IR (KBr): 3250, 2900, 1650, 1580, 1440, 1300, 1090 cm$^{-1}$.

$^1$H-NMR (DMSO-d$_6$) δ: 1.43–1.76 (1H,m), 1.98 (2H,t,J=7.5 Hz), 1.80–2.10 (1H,m), 2.13–2.40 (2H,m), 2.67 (2H,t, J=9 Hz), 2.90–3.23 (2H,m), 3.33–3.60 (1H,m), 4.10–4.43 (1H,m), 7.28 (2H,d,J=9 Hz), 7.75 (2H,d,J=9 Hz).

Working Example 16

Production of N-[4-[3-(2,4-diamino-5,6-dihydropyrrolo[2,3-d]pyrimidin-5-yl)propyl]benzoyl]L-glutamtic acid The compound (41 mg) obtained in the Working Example 13 was subjected to the same reaction as that in the Working Example 14, to give the object compound (32 mg).

IR (KBr): 3700–2350, 3215, 1690–1620, 1540 cm$^{-1}$.

$^1$H-NMR (Me$_2$SO -d$_6$) δ: 1.02–1.85 (4H,m), 1.85–2.83 (6H,m), 2.90–3.30 (2H,m), 3.55 (1H,t,J=11 Hz), 4.15–4.45 (1H,m), 6.38 (2H,brs), 6.77 (2H,brs), 6.90 (1H,brs), 7.22 (2H,d,J=8 Hz), 7.74 (2H,d,J=8 Hz), 8.22 (1H,d,J=7 Hz).

Working Example 17

Production of tert-butyl 4-[3-(2,4-diamino-6-hydroxy-7H-pyrrolo[2,3-d]pyrimidin-5-yl)-1-methylpropyl]benzoate:

The compound (3.18 g) obtained in the Reference Example 19 was subjected to the same reaction as that in the Working Example 1, to give the object compound (2.61 g).

IR (KBr): 3360, 3235, 2975, 2700, 1715, 1625, 1584 1438, 1290, 1163, 1118, 848 cm$^{-1}$.

$^1$H-NMR (Me$_2$SO-d$_6$) δ: 1.14 (3H,d,J=7 Hz), 1.20–1.50 (2H,m), 1.54 (9H,s), 1.55–1.80 (1H,m), 1.80–2.05 (1H,m), 2.60–2.78 (1H,m), 3.20–3.30 (1H,m), 5.86 (2H,brs), 5.96 (2H,brs), 7.25 (2H,d,J=8 Hz), 7.81 (2H,d,J=8 Hz), 10.42 (1H,s).

Working Example 18

Production of tert-butyl 4-[3-(2,4-diamino-6,7-dihydro-5H-pyrrolo[2,3-d]pyrimidin-5-yl)-1-methylpropyl]benzoate (A) and tert-butyl-4-[3-(2,4-diamino-7H-pyrrolo-[2,3-d]pyrimidin-5-yl)-1-methyl-propyl]benzoate (B):

To a suspension of the compound (2.00 g) obtained in the Working Example 17 in tetrahydrofuran (25 ml) was a solution of boiane-tetrahydrofuran complex (40.3 mmol) tetrahydrofuran (40.3 ml). After stirring for 10 minutes, the mixture was cooled to room temperature and further stirred for 5 hours. To the reaction mixture was added an acetic acid-methanol mixture (1:1, 40 ml) and the mixture was stirred for 18 hours at room temperature. After evaporation of solvent under reduced pressure, the resulting residue was purified by column chromatography (carrier: silica gel, 100 g, developing solvent; dichloromethane-ethanol=20:1→25:2, then dichloromethane-ethanol containing ammonia (6%)), to give the object compound (A) (579 mg) and (B) (1.214 g).

(A) IR (KBr): 3350, 3200, 2980, 2940m, 1714, 1650, 1608, 1290, 1163, 1115, 848 cm$^{-1}$.

$^1$H-NMR (CDCl$_3$) δ: 1.31 (3H,d,J=7 Hz), 1.60 (9H,s), 1.94 (2H,dt,J=8 Hz,8 Hz), 2.40–2.60 (2H,m), 2.85 (1H,tq, J=7 Hz,7 Hz) , 4.50–5.50 (4H,br), 6.46 (1H,s), 7.27 (2H,d, J=8 Hz), 7.96 (2H,d,J=8 Hz), 9.20 (1H,brs).

(B) IR (KBr): 3340, 3195, 2980, 2935, 1715, 1507, 1430, 1295, 1163, 1115, 847 cm$^{-1}$.

$^1$H-NMR (Me$_2$SO-d$_6$) δ: 1.18 (2.25H,d,J=7 Hz), 1.19 (0.75H,d,J=7 Hz), 1.23–1.42 (2H,m), 1.45–1.65 (2H,m), 1.54 (9H,s), 2.54–2.70 (1H,m), 2.90–3.08 (2H,m), 3.30–3.50 (1H,m), 5.43 (4H,s), 5.95 (0.25H,s), 6.00 (0.75H, s), 7.32 (2H,d,J=8 Hz), 7.82 (2H,d,J=8 Hz).

Working Example 19

Production of diethyl N-[4-[3-(2,4-diamino-6,7-dihydro-5H-pyrrolo[2,3-d]pyrimidin-5-yl)-1-methylpropyl]benzoyl] -L-glutamate The compound (A) (581 mg) obtained in the Working Example 18 was subjected to the same reaction as that in the Working Example 3 to give the object compound (640 mg).

IR (KBr): 3375, 3200, 2975, 2930, 1738, 1608, 1430 1200, 1008, 853 cm$^{-1}$.

$^1$H-NMR (Me$_2$SO-d$_6$) δ: 1.17 (3H,t,J=7 Hz), 1.18 (3H,d, J=7 Hz), 1.19 (3H,t,J=7 Hz), 1.26–1.44 (2H,m), 1.44–1.63 (2H,m), 1.90–2.20 (2H,m), 2.44 (2H,t,J=7 Hz), 2.63–2.80 (1H,m), 2.90–3.08 (2H,m), 3.30–3.50 (1H,m), 4.05 (2H,q, J=7 Hz), 4.11 (2H,g,J=7 Hz), 4.37–4.50 (1H,m), 5.36 (2H, s), 5.37 (2H,s), 5.87 (0.25H,s), 5.91 (0.75H,s), 7.30 (2H,d, J=8 Hz), 7.80 (2H,d,J=8 Hz), 8.66 (1H,d,J=8 Hz).

Working Example 20

Production of N-[4-[3-(2,4-diamino-6,7-dihydro-5H-pyrrolo[2,3-d]pyrimidin-5-yl)-t-methylpropyl]benzoyl]-L-glutamic acid:

The compound (600 mg) obtained in the working Example 19 was subjected to the same reaction as that in the Working Example 4, to give the object compound (508 mg).

IR (KBr): 3350, 3200, 1690, 1680–1610, 1635, 1530, 1400, 1300, 853 cm$^{-1}$.

$^1$H-NMR (Me=SO-d$_6$) δ: 1.20 (3H,d,J=7 Hz), 1.25–1.65 (4H,m), 1.87–2.20 (2H,m), 2.30 (2H,t,J=7 Hz), 2.60–2.80 (1H,m), 3.00–3.20 (2H.,m), 3.42–3.60 (1H,m), 4.22–4.40 (1H 6.20–5.08 (5H,m), 7.28 (2H,d,J=8 Hz), 7.78 (2H,d,J=8 Hz), 8.28–8.36 (1H,m).

Working Example 21

Production of diethyl N-[4-[3-(2,4-diamino-7H-pyrrolo [2,3-d]pyrimidin-5-yl)-1-methylpropyl]benzoyl]L-glutamic acid:

The compound (B) (540 mg) obtained in the Working Example 18 was subjected to the same reaction as that in the Working Example 3, to give the object compound (556 mg).

IR (KBr): 3340, 3180, 2935, 1735, 1640, 1610, 1580, 1200, 1095, 1018, 850 cm$^{-1}$.

$^1$H-NMR (CDCl$_3$) δ: 1.23 (3H,t,J=7 Hz), 1.30 (3H,d,J=7 Hz), 1.31 (3H,t,J=7 Hz), 1.80–2.05 (4H,m), 2.15–2.57 (4H, m), 2.83 (1H,tq,J=7 Hz,7 Hz), 4.12 (2H,q,J=7 Hz), 4.25 (2H,q,J=7 Hz), 4.68 (2H,brs), 4.75–4.87 (1H,m), 4.92 (2H, brs), 6.43 (1H,s), 7.26 (2H,d,J=8 Hz), 7.37 (1H,dd,J=7 Hz,3 Hz), 7.77 (2H,d,J=8 Hz), 8.81 (1H,brs).

Working Example 22

Production of N-[4-[3-(2,4-diamino-7H-pyrrolo[2,3-d] pyrimidin-5-yl)-t-methylpropyl]benzoyl]-L-glutamic acid:

The compound (533 mg) obtained in the Working Example 21 was subjected to the same reaction as that in the Working Example 4, to give the object compound (436 mg).

IR (KBr): 3350, 3205, 1650, 1540, 1540, 1400, 850 cm$^{-1}$.

$^1$H-NMR (Me$_2$SO-d$_6$) δ: 1.25 (3H,d,J=7 Hz), 1.73–2.20 (4H,m), 2.35 (3H,t,J=8 Hz), 2.40–2.68 (2H,m), 2.85 (1H, tg,J=7 Hz,7 Hz), 4.32–4.45 (1H,m), 5.54 (2H,brs), 6.06 (2H,brs), 6.38 (1H,s), 7.33 (2H,d,J=8 Hz), 7.83 (2H,d,J=8 Hz), 8.49 (1H,d,J=8 Hz), 10.45 (1H,s).

Working Example 23

The compound (50 mg per tablet) obtained in the Working Example 14, lactose (250 mg per tablet), corn starch (51 mg per tablet) and hydroxypropylcellulose L (9 mg per tablet) were mixed according to the conventional method and granulated. The granules, corn starch (8 mg per tablet) and magnesium stearate (2 mg per tablet) were mixed and tabletted according to the conventional method, to give tablets (370 mg per tablet).

Working Example 24

Ten grams of the sodium salt of the compound obtained in the Working Example 14 was dissolved in 1 l of physiological saline. The solution was filerted through a microfilter and dispensed in 2.2 ml aliquots in ampoules, sterilized at 110° C. for 30 minutes and the ampoules may be used for subcutaneous, intravenous or intramuscular injections.

Working Example 25

Five grams of the hydrochloride of the compound obtained in the Working Example 14 and 10 g of mannitol were dissolved in 1 l of distilled water, and the solution was dispensed in 2 ml aliquots into ampules after filtration through a bacterial filter. The ampoules were dried in a freeze-drier and sealed, and thus the ampoules of which content is dissolved before use were obtained. Before use for injection, the ampoules are opened and the content is dissolved in, for example, 2 ml of physiological saline.

What is claimed is:

1. A method for producing a compound of the formula

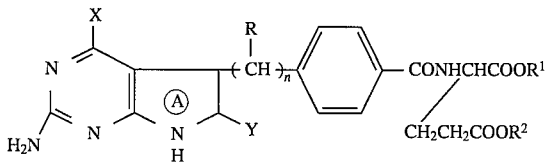

wherein the ring Ⓐ is a pyrrole or pyrroline ring, X is an amino group or a hydroxyl group, Y is a hydrogen atom, an amino group or a hydroxyl group, R is a hydrogen atom, a fluorine atom, an alkyl group, an alkenyl group or an alkynyl group, —COOR$^1$ and COOR$^2$ are a carboxyl group which may be esterified and n is an integer of 2 to 4, and R may be different in each of the n repeating units, or salts thereof, which comprises reacting a compound of the formula

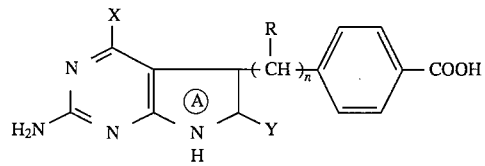

wherein the ring Ⓐ, X, Y, R and n are the same as defined above, a reactive derivative at the carboxyl group or a salt thereof, with a compound of the formula

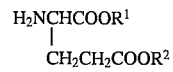

wherein —COOR$^1$ and —COOR$^2$ are the same as defined above.

* * * * *